US010815219B2

(12) United States Patent
Wang et al.

(10) Patent No.: US 10,815,219 B2
(45) Date of Patent: Oct. 27, 2020

(54) 2,4-DIAMINOQUINAZOLINE DERIVATIVES FOR INHIBITING ENDOPLASMIC RETICULUM (ER) STRESS

(71) Applicant: The Board of Regents of the University of Oklahoma, Norman, OK (US)

(72) Inventors: Weidong Wang, Edmond, OK (US); Jae Wook Lee, Gangwon-do (KR)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 16/047,372

(22) Filed: Jul. 27, 2018

(65) Prior Publication Data

US 2019/0047988 A1 Feb. 14, 2019

Related U.S. Application Data

(60) Provisional application No. 62/542,408, filed on Aug. 8, 2017.

(51) Int. Cl.
| | | |
|---|---|---|
| *C07D 403/04* | (2006.01) | |
| *A61K 47/51* | (2017.01) | |
| *C07D 401/04* | (2006.01) | |
| *A61P 39/00* | (2006.01) | |

(52) U.S. Cl.
CPC ............ *C07D 403/04* (2013.01); *A61K 47/51* (2017.08); *A61P 39/00* (2018.01); *C07D 401/04* (2013.01)

(58) Field of Classification Search
None
See application file for complete search history.

(56) References Cited

U.S. PATENT DOCUMENTS

2010/0130476 A1* 5/2010 Wang ................. A61K 31/4422
514/218

FOREIGN PATENT DOCUMENTS

WO WO2009001060 * 12/2008

OTHER PUBLICATIONS

Sarvani et al., Unraveling the role of ER stress inhibitors in the context of metabolic diseases. Pharmacological Research, 2017, 119, 412-421.*
Schafer, S., Kolkhof, P. Failure is an option: learning from unsuccessful proof-of-concept trials. Drug Discovery Today. Nov. 2008, 13, 913-916.*
Honig, H., Pullman, W. From bench to clinic and back: Perspective on the 1st IQPC Translational Research conference. Journal of Translational Medicine. Dec. 2004, 2, 44.*
Duan et al., Discovery, Synthesis, and Evaluation of 2,3-Diaminoquinazolines as a Novel Class of Pancreatic β-Cell-Protective Agents against Endoplasmic Reticulum (ER) Stress. Journal of Medicinal Chemistry, 2016, 59, 7783-7800.*
Schuit, F.C., et al.; "Glucose stimulates proinsulin biosynthesis by a dose-dependent recruitment of pancreatic beta cells"; Proc. Natl. Acad. Sci. USA; Jun. 1988; 85; 3865-3869.
Olson, L.K., et al.; "Chronic exposure of HIT cells to high glucose concentrations paradoxically decreases insulin gene transcription and alters binding of insulin gene regulatory protein"; J. Clin. Invest.; 1993; 92(1); 514-519.
Sharma, A., et al.; "The Reduction of Insulin Gene Transcription in HIT-T15 Beta Cells Chronically Exposed to High Glucose Concentration is Associated with the Loss of RIPE3b1 and STF-1 Transcription Factor Expression"; Mol. Endocrinol.; 1995; 9; 1127-1134.
Poitout, V., et al.; "Chronic exposure of betaTC-6 cells to supraphysiologic concentrations of glucose decreases binding of the RIPE3b1 insulin gene transcription activator"; J. Clin. Invest.; 1996; 97(4); 1041-1046.
Slee, E.A., et al; "Ordering the Cytochrome c-Initiated Caspase Cascade: Hierarchical Activation of Caspases-2, -3, -6, -7, -8, and -10 in a Caspase-9-dependent Manner"; J. Cell. Biol.; Jan. 1999, 144(2); 281-292.
Bertolotti, A., et al.; "Dynamic interaction of BiP and ER stress transducers in the unfolded-protein response"; Nat. Cell Biol.; Jun. 2000; 2; 326-332.
Herceg, Z., et al.; "Functions of poly(ADP-ribose) polymerase (PARP) in DNA repair, genomic integrity and cell death"; Mutation Research; 2001; 477; 97-110.
Kaneto, H., et al.; "Involvement of c-Jun N-terminal Kinase in Oxidative Stress-mediated Suppression of Insulin Gene Expression"; J. Biol. Chem.; Aug. 2002; 277(33); 30010-30018.
Kataoka, K., et al.; "MafA is a Glucose-regulated and Pancreatic Beta-Cell-specific Transcriptional Activator for the Insulin Gene"; J. Biol. Chem.; Dec. 2002; 277(51); 49903-49910.
Kahn, S.E.; "The relative contributions of insulin resistance and beta-cell dysfunction to the pathophysiology of Type 2 diabetes"; Diabetologia; 2003; 46; 3-19.
Donath, M.Y., et al.; "Decreased beta-cell mass in diabetes: significance, mechanisms and therapeutic implications"; Diabetologia; 2004; 47; 581-589.
Anderson, M.S., et al.; "The NOD Mouse: A Model of Immune Dysregulation"; Ann. Rev. Immunol.; 2005; 23; 447-485.
Lipson, K.L.; "Regulation of insulin biosynthesis in pancreatic beta cells by an endoplasmic reticulum-resident protein kinase IRE1"; Cell Metabolism; Sep. 2006; 4; 245-254.
Van Lommel, L., et al.; "Probe-Independent and Direct Quantification of Insulin mRNA and Growth Hormone mRNA in Enriched Cell Preparations"; Diabetes; Dec. 2006; 55; 3214-3220.
Prentki, M., et al.; "Islet Beta cell failure in type 2 diabetes"; J. Clin. Invest.; 2006; 116(7); 1802-1812.
Lipson, K.L., et al.; "The Role of IRE1alpha in the Degradation of Insulin mRNA in Pancreatic Beta-Cells"; PLoS One; Feb. 2008; 3(2); 1-7.

(Continued)

*Primary Examiner* — Po-Chih Chen
(74) *Attorney, Agent, or Firm* — Hall Estill Law Firm

(57) ABSTRACT

Novel 2,4-diaminoquinazoline derivatives are disclosed. The compounds can be used in treating diseases and conditions which are associated with abnormal cell function related to endoplasmic reticulum (ER) stress. For example, the compounds can be used as suppressors of ER stress-induced pancreatic β-cell dysfunction and death, for example in the treatment of diabetes.

34 Claims, 12 Drawing Sheets
(2 of 12 Drawing Sheet(s) Filed in Color)

(56) References Cited

OTHER PUBLICATIONS

Muoio, D.M., et al.; "Mechanisms of Disease:Molecular and metabolic mechanisms of insulin resistance and Beta-cell failure in type 2 diabetes"; Nat. Rev., Mol. Cell Biol.; Mar. 2008; 9; 193-205.

Han, D., et al.; "IRE1alpha Kinase Activation Modes Control Alternate Endoribonuclease Outputs to Determine Divergent Cell Fates"; Cell; Aug. 7, 2009; 38; 562-575.

Von Herrath, M., et al.; "Animal models of human type 1 diabetes"; Nat. Immunol.; Feb. 2009; 10(2); 129-132.

Fonseca, S.G., et al.; "Endoplasmic reticulum stress and pancreatic Beta-cell death"; Trends Endocrinol. Metab.; Jul. 2011; 22(7); 266-274.

Oslowski, C.M., et al.; "Measuring ER Stress and the Unfolded Protein Response Using Mammalian Tissue Culture System"; Methods Enzymol.; 2011; 490; 71-92.

Back, S.H., et al.; "Endoplasmic Reticulum Stress and Type 2 Diabetes"; Annu. Rev. Biochem.; 2012; 81; 767-793.

Papa, F.R.; "Endoplasmic Reticulum Stress, Pancreatic Beta-Cell Degeneration, and Diabetes"; Cold Spring Harb. Perspect. Med.; 2012; 2; 1-18.

Wang, S., et al.; "The impact of the unfolded protein response on human disease"; J. Cell Biol.; Jun. 25, 2012; 197 (7); 857-867.

Hetz, C., et al.; "Targeting the unfolded protein response in disease"; Nat. Rev. Drug Discov.; Sep. 2013; 12; 703-719.

Van Horn, K.S., et al.; "Antibacterial Activity of a Series of N2,N4-Disubstituted Quinazoline-2,4-diamines"; J. Med. Chem.; 2014; 57; 3075-3093.

Vetere, A., et al.; "Targeting the pancreatic Beta-cell to treat diabetes"; Nat. Rev. Drug Discov.; Apr. 2014; 13; 278-289.

Rutter, G.A., et al.; "Pancreatic Beta-cell identity, glucose sensing and the control of insulin secretion"; Biochem. J.; 2015; 466; 203-218.

Wang, P., et al.; "Diabetes mellitus—advances and challenges in human Beta-cell proliferation"; Nat. Rev. Endocrinol.; Apr. 2015; 11; 201-212.

* cited by examiner

Scheme 1

Scheme 2

Scheme 3

Scheme 4

Scheme 5

A

B

2,4-DIAMINOQUINAZOLINE DERIVATIVES FOR INHIBITING ENDOPLASMIC RETICULUM (ER) STRESS

CROSS-REFERENCE TO RELATED APPLICATIONS

The present application claims priority under 35 U.S.C. § 119(e) to U.S. Ser. No. 62/542,408, filed Aug. 8, 2017, the entirety of which is hereby expressly incorporated by reference herein.

GOVERNMENT SUPPORT

This invention was made with government support under Contract Number GM103636 awarded by the National Institutes of Health (NIH). The government has certain rights in the invention.

BACKGROUND

Diabetes, a group of metabolic diseases in which blood sugar levels are abnormally high over a prolonged period, has become a serious public health problem with tremendous social and economic burden on society. As of 2015, 415 million people worldwide were estimated to suffer from have diabetes. The dysfunction and death of insulin-producing pancreatic β-cells are critical elements in the pathogenesis of type 1 (T1D) and type 2 (T2D) diabetes. Increasing evidence indicates that endoplasmic reticulum (ER) stress, a condition in which misfolded proteins accumulate in the ER, plays an important role in the decline in pancreatic β-cell function and mass in diabetes. Thus, prevention of functional pancreatic β-cell death by mitigating ER stress is a promising therapeutic approach for patients with diabetes. Unfortunately, no existing anti-diabetic drugs have been known that are capable of halting the progression of β-cell dysfunction and death.

In T2D, β-cells are forced to synthesize more insulin due to higher metabolic demands of obesity and insulin resistance, which typically exceeds the cellular capacity of the ER for protein folding, and eventually leads to ER stress and β-cell dysfunction and death. In addition, the common causes for β-cell dysfunction and death in T2D, including lipotoxicity, glucotoxicity, oxidative stress, amyloid deposition, and insulin mutations, have been known to be associated with unresolvable chronic ER stress. In T1D in which β-cells are destroyed by an auto-immune reaction, ER stress has also been implicated, and an ER stress-reducing chemical chaperone has been reported to prevent the onset of T1D in mouse models by protecting β-cell survival.

ER stress induces activation of the unfolded protein response (UPR) through three ER membrane proteins, inositol-requiring protein 1α (IRE1α), PKR-like ER kinase (PERK), and activating transcription factor 6 (ATF6), which act as unfolded protein sensors. In unstressed cells, these sensors are maintained in an inactive state through interaction with the protein chaperone binding immunoglobulin protein (BiP). Under ER stress, unfolded and misfolded proteins accumulate in the ER and bind to and sequester BiP, thereby releasing and activating the sensors. Upon initial or mild ER stress, IRE1α, PERK, and ATF6 each activate a series of events aimed at restoring ER homeostasis by altering the translation, folding, and post-translational modification of secreted and membrane proteins. However, failure to adequately re-establish ER homeostasis eventually triggers cell death, as in the case of chronic or severe ER stress.

Despite the importance of ER stress in mediating β-cell dysfunction and death in the pathogenesis of diabetes, only a handful of small molecules have so far been reported to exhibit β-cell-protective activities against ER stress. A major reason for the scarcity of β-cell-protective small molecules could lie in the unique property of β-cells. β-cells normally produce and rapidly secrete insulin in response to increases in blood glucose levels after food intake. To achieve this, they maintain a very large pool of proinsulin mRNA (~20% of the total cellular mRNA) and increase proinsulin protein synthesis 25-fold upon glucose stimulation. This surge in proinsulin synthesis places a heavy burden on the protein-folding capacity of the ER; β-cells are therefore particularly susceptible to ER stress. This β-cell property may also in part explain why compounds that protect other cell types from ER stress fail to protect β-cells. Furthermore, the existing β-cell-protective small molecules still suffer from the issue of low potency, often with $EC_{50}$ values ranging from single- to double-digit μM. New high potency small molecules for protecting pancreatic β-cell mass are thus greatly desired.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure. The patent or application file contains at least one drawing executed in color. Copies of this patent or patent application publication with color drawing(s) will be provided by the Office upon request and payment of the necessary fee.

DETAILED DESCRIPTION

Figure 1A:
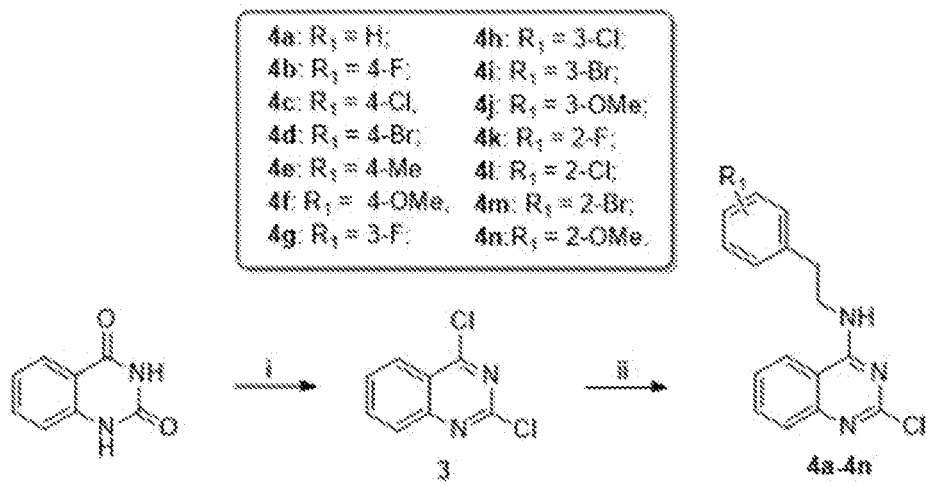
FIG. 1A shows schemes for the synthesis of 2,4-diaminoquinazoline derivatives 4a-4n and 5a-5m. Scheme 1: Synthesis of 2,4-diaminoquinazoline derivative compounds 4a-n. Reagents and conditions used were: (reaction i) dimethylaniline, POCl₃, 120° C., 24 hrs, 69%; and (reaction ii) aryl amine, DIEA, n-BuOH, 40° C., 2 hrs, 65-85%. Scheme 2: Synthesis of 2,4-diaminoquinazoline derivative compounds 5a-m. Reagents and conditions used were: (reaction iii) L-prolinol, DIEA, n-BuOH, 120° C., overnight, 50-85%.
Figure 1A:
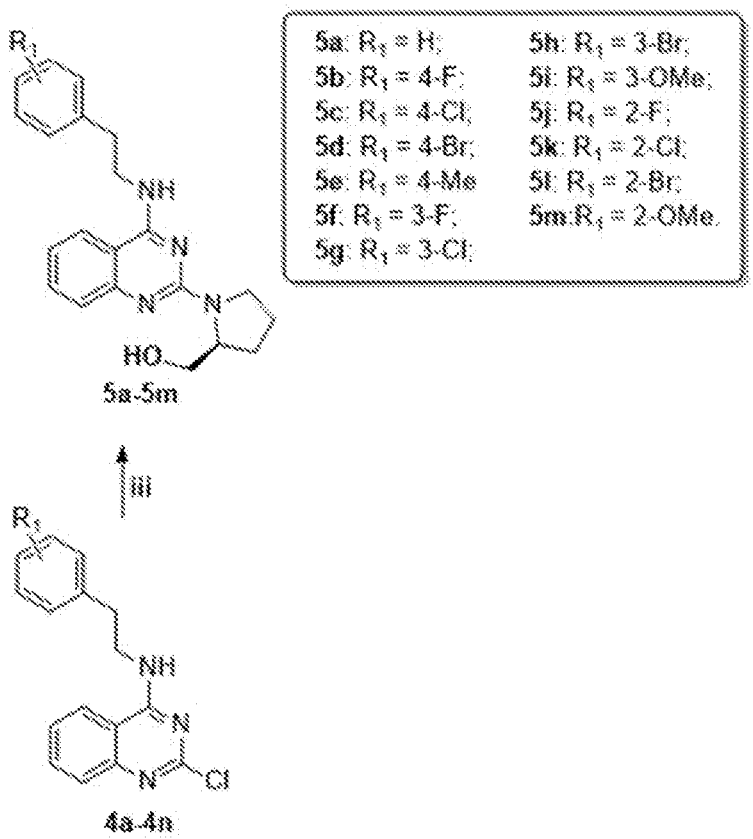

The present disclosure is directed to novel 2,4-diaminoquinazoline derivatives. The compounds are effective in inhibiting ER stress. For example, the compounds can be used as potent suppressors of ER stress-induced β-cell death and dysfunction. In at least one non-limiting embodiment for example, the derivative compound (1-(4-((4-methoxybenzyl)amino)quinazolin-2-yl)piperidin-2-yl)methanol has 80% maximum rescue activity and an $EC_{50}$ of 0.56 μM against ER stress. Further, the compound alleviates ER stress/UPR response by inhibiting Tm-induced up-regulation of all three branches of UPR and apoptosis.

Before further describing various embodiments of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods and application and uses thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, published patent applications (including U.S. Ser. No. 62/542,408), and non-patent publications including published articles mentioned in the specification or referenced in any portion of this application, are herein expressly incorporated by reference in their entirety to the same extent as if each individual patent or publication was specifically and individually indicated to be incorporated by reference.

The following abbreviations may be used herein: Tm, tunicamycin; ER, endoplasmic reticulum; STAT1, signal transducer and activator of transcription 1; INS-1 cell, rat insulinoma cell line; DIEA, N,N-diisopropylethylamine; UPR, unfolded protein response; SAR, structure-activity relationship; $EC_{50}$, half maximal effective concentration; RT-PCR, reverse transcription polymerase chain reaction; BFA, brefeldin A; CHOP, C/EBP homologous protein; PARP, Poly(ADP-ribose) polymerase; eIF2α, eukaryotic translation initiator factor 2α. TUNEL, Terminal deoxynucleotidyl transferase dUTP nick end labeling; GSIS, Glucose Stimulated Insulin Secretion; PERK, PKR-like ER kinase; XBP1, X-box binding protein 1; ATF6, activating transcription factor 6; ATF4, activating transcription factor 4; FBS, fetal bovine serum; PDX1, pancreatic and duodenal homeobox 1; MafA, v-maf musculoaponeurotic fibrosarcoma oncogene family, protein A; INS1, insulin 1; INS2, insulin 2.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

The term "active agent" as used herein refers to 2,4-diaminoquinazoline derivative compounds as described herein or active conjugates thereof. A conjugate is a compound comprising an active agent covalently linked, directly or indirectly via a linker molecule, to a secondary compound, such as an antibody or fragment thereof. The active agent may be associated with a targeting moiety or molecule which is able to bind to a target cell or a portion of a target cell. The targeting moiety may be linked directly or indirectly to the active agent, or to the pharmaceutically acceptable carrier, vehicle, or diluent which contains or is associated with the active agent. The targeting moiety may be any molecule that can bind to another molecule. For example, a targeting moiety may include an antibody or its antigen-binding fragments, a receptor molecule, a chimeric antibody molecule, or an affinity reagent. As used herein, the term "targeting moiety" refers to a structure that binds or associates with a biological moiety or fragment thereof. As noted, in some embodiments, the targeting moiety may be an antibody. In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the active agent to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the active agent of the present disclosure may be designed to provide delayed, controlled, extended, and/or sustained release using formulation techniques which are well known in the art.

The term "topical" is used herein to define a mode of administration through an epithelial surface, such as but not limited to, a material that is administered by being applied externally to the eye. A non-limiting example of topical administration is through the use of eyedrops.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of the active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one". Where used herein, the pronoun "we" is intended to refer to all persons involved in a particular aspect of the investigation disclosed herein and as such may include non-inventor laboratory assistants and collaborators working under the supervision of the inventor.

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc., all the way down to the number one (1); and less than 10 includes 9, 8, 7, etc., all the way down to the number one (1).

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the active agent or composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

By "biologically active" is meant the ability of the active agent to modify the physiological system of an organism without reference to how the active agent has its physiological effects.

Effectiveness of a method or use, such as a treatment that provides a potential therapeutic benefit or improvement of a condition or disease, can be ascertained by various methods and testing assays.

The active agents disclosed herein can be used in the treatment of type 1 and type 2 diabetes, and other diseases or conditions involving ER stress, including neurodegenerative diseases such as Parkinson's disease, amyotrophic lateral sclerosis (ALS), Alzheimer's disease (AD), Huntington's disease, and progressive supra nuclear palsy (PSP). Other indications also include metabolic syndrome including obesity, atherosclerosis, chronic heart disease, stroke, ischemia-reperfusion injury, and cancer.

The active agents of the present disclosure may be present in the pharmaceutical compositions at any concentration that allows the pharmaceutical composition to function in accordance with the present disclosure; for example, but not by way of limitation, the active agents may be present in the composition in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Suitable carriers, vehicles, and other components that may be included in the formulation are described, for example, in *Remington: The Science and Practice of Pharmacy*, $21^{st}Ed.$ and $22^{nd} Ed.$ The term "pharmaceutically acceptable" means that the carrier is a non-toxic material that does not interfere with the effectiveness of the biological activity of the active agent. The characteristics of the carrier will depend on various factors, including but not limited to, the route of administration.

For example, but not by way of limitation, the active agent may be dissolved in a physiologically acceptable pharmaceutical carrier or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the active agent and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the present disclosure may include the incorporation or entrapment of the active agent in various types of drug delivery systems that function to provide targeted delivery, controlled release, and/or increased half-life to the active agent. For example, but not by way of limitation, it is possible to entrap the active agent in microcapsules prepared by coacervation techniques or by interfacial polymerization (for example, hydroxymethylcellulose or gelatin-microcapsules and poly-(methylmethacylate) microcapsules, respectively). It is also possible to entrap the active agent in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the active agent of the present disclosure may be incorporated into particles of one or more polymeric materials, as this type of incorporation can be useful in controlling the duration of action of the active agent by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(l-aspartamide), and combinations thereof.

The pharmaceutical compositions described or otherwise contemplated herein may further comprise at least one delivery agent, such as a targeting moiety, that assists in delivery of the active agent to a desired site of delivery, such as a pancreatic beta cell.

The compositions of the present disclosure may be formulated for administration by any other method known or otherwise contemplated in the art, as long as the route of administration allows for delivery of the active agent so that the compounds can function in accordance with the present disclosure, e.g., to reduce ER stress. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically acceptable carrier, vehicle, diluent, or other agent for mixing with the active agent for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a worldwide web page accessible via the internet.

The kit may contain single or multiple doses of the pharmaceutical composition which contains the active agent. When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of the active agent calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent may sometimes be a minor component (from about 0.1 to about 50% by weight, such as but not limited to, from about 1 to about 40% by weight) with the remainder being various vehicles or carriers and processing aids helpful for forming the desired dosing form.

The active agent may be provided as a "pharmaceutically acceptable salt," which refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297 (incorporated by reference herein in its entirety).

The amount of the active agent that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific diseases or other conditions involved; the degree, involvement, and/or severity of the diseases or conditions; the response of the individual subject; the particular active agent administered; the mode of administration; the bioavailability characteristics of the preparation administered; the dose regimen selected; the use of concomitant medication; and other relevant circumstances. A therapeutically effective amount of an active agent of the present disclosure also refers to an amount of the active agent which is effective in controlling, reducing, or ameliorating the condition to be treated.

Practice of the method of the present disclosure may include administering to a subject a therapeutically effective amount of the pharmaceutical composition (containing the active agent in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Compositions of the active agent can be administered in a single dose treatment or in multiple dose treatments on a schedule and over a time period appropriate to the age, weight and condition of the subject, the particular composition used, and the route of administration. In one embodiment, a single dose of the composition according to the disclosure is administered. In other embodiments, multiple doses are administered. The frequency of administration can vary depending on any of a variety of factors, e.g., severity of the symptoms, degree of immunoprotection desired, or whether the composition is used for prophylactic or curative purposes. For example, in certain embodiments, the composition is administered once per month, twice per month, three times per month, every other week, once per week, twice per week, three times per week, four times per week, five times per week, six times per week, every other day, daily, twice a day, or three times a day. The duration of treatment, e.g., the period of time over which the composition is administered, can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) or vehicle to form a pharmacological composition. Pharmaceutically acceptable carriers can contain a physiologically acceptable compound that acts to, e.g., stabilize, or increase or decrease the absorption or clearance rates of the pharmaceutical compositions. Physiologically acceptable carriers and vehicles can include, for example, carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds, carriers, and vehicles include wetting agents, emulsifying agents, dispersing agents or preservatives.

When administered orally, the present compositions may be protected from digestion. This can be accomplished either by complexing the active agent with a composition to render it resistant to acidic and enzymatic hydrolysis or by packaging active agent in an appropriately resistant carrier such as a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical, transdermal administration, the agents are formulated into ointments, creams, salves, powders and gels. Transdermal delivery systems can also include, e.g., patches. The present compositions can also be administered in sustained delivery or sustained release mechanisms. For example, biodegradeable microspheres or capsules or other biodegradeable polymer configurations capable of sustained delivery of the active agent can be included herein.

For inhalation, the active agent can be delivered using any system known in the art, including dry powder aerosols, liquids delivery systems, air jet nebulizers, propellant systems, and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

The active agent can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa).

In one aspect, the pharmaceutical formulations comprising the active agent are incorporated in lipid monolayers or bilayers, e.g., liposomes, such as shown in U.S. Pat. Nos. 6,110,490; 6,096,716; 5,283,185; and 5,279,833. Liposomes and liposomal formulations can be prepared according to standard methods and are also well known in the art, such as U.S. Pat. Nos. 4,235,871; 4,501,728 and 4,837,028.

In one aspect, the active agent is prepared with one or more carriers that will protect the active agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The active agent in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active agent is combined in a mixture with one or more pharmaceutically suitable excipients. Sterile phosphate-buffered saline is one example of a pharmaceutically suitable excipient.

Examples of routes of administration of the active agents described herein include parenteral injection, e.g., by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising the active agent can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The active agents may be administered in solution. The formulation thereof may be in a solution having a suitable pharmaceutically acceptable buffer such as phosphate, Tris (hydroxymethyl) aminomethane-HCl or citrate, and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

For example, but not by way of limitation, the therapeutically effective amount of an active agent used in the present disclosure will generally contain sufficient active agent to deliver in a range of from about 0.01 µg/kg to about 10 mg/kg (weight of active agent/body weight of patient). For example, but not by way of limitation, the composition will deliver about 0.1 µg/kg to about 5 mg/kg, and more particularly about 1 µg/kg to about 1 mg/kg.

Exemplary, non-limiting ranges for a therapeutically or prophylactically effective amount of the active agent include but are not limited to 0.001 mg/kg of the subject's body weight to 100 mg/kg of the subject's body weight, more typically 0.01 mg/kg to 100 mg/kg, 0.1 mg/kg to 50 mg/kg, 0.1 mg/kg to 40 mg/kg, 1 mg/kg to 30 mg/kg, or 1 mg/kg to 20 mg/kg, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg, or 5 mg to 1500 mg, as a fixed dosage.

The composition is formulated to contain an effective amount of the active agent, wherein the amount depends on the animal to be treated and the condition to be treated. In certain embodiments, the active agent is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 40 pg to about 300 pg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

The dosage of an administered active agent for humans will vary depending upon such factors as the patient's age, weight, height, sex, general medical condition and previous medical history. In certain non-limiting embodiments, the recipient is provided with a dosage of the active agent that is in the range of from about 1 mg to 1000 mg as a single infusion or single or multiple injections, although a lower or higher dosage also may be administered. The dosage may be in the range of from about 25 mg to 100 mg of the active agent per square meter ($m^2$) of body surface area for a typical adult, although a lower or higher dosage also may be administered. Examples of dosages that may be administered to a human subject further include, for example, 1 to 500 mg, 1 to 70 mg, or 1 to 20 mg, although higher or lower doses may be used. Dosages may be repeated as needed, for example, once per week for 4-10 weeks, or once per week for 8 weeks, or once per week for 4 weeks. It may also be given less frequently, such as every other week for several months, or more frequently, such as twice weekly or by continuous infusion.

Where used herein alkyls, alkoxyls, haloalkyls, and haloalkoxyls are generally intended to refer to molecules having hydrocarbon chains that comprise 1, 2, 3, 4, 5, 6, 7, 8, 9, 10, 11, or 12 carbons, unless otherwise designated. The hydrocarbon chains may be straight or branched. Examples of alkyls include but are not limited to methyl, ethyl, propyl, isopropyl, and butyl. Alkoxy denotes an alkyl group which is linked to an oxygen atom. Examples of alkoxyls include but are not limited to methoxyl, ethoxyl, propoxyl, isopropoxyl, and butoxyl. Haloalkyls and haloalkoxyls are alkyls and alkoxyls which comprise at least one halogen atom such as chlorine, fluorine, bromine, or iodine.

EXAMPLES

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

In at least certain embodiments, the present disclosure includes compounds and methods of treating disorders and conditions related to ER stress, including, but not limited to type 1 diabetes and type 2 diabetes (or others disorders or conditions described elsewhere herein). The compound may be an 2,4-diaminoquinazoline derivative compound having the chemical structure I:

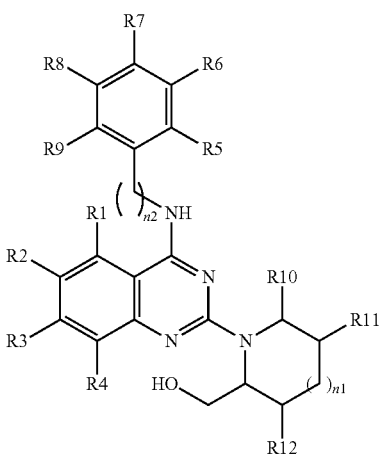

I wherein, in at least certain embodiments, the $R_1$-$R_{12}$ substituents of chemical structure I are independently selected from, but not limited to, the group consisting of hydrogen (H), hydroxyl (OH), halogens (halos) including chlorine (Cl), fluorine (F), bromine (Br), iodine (I), alkyls, alkoxys, haloalkyls (including mono, di, and trihaloalkyls), and haloalkoxyl (including mono, di, and trihaloalkoxyls), and n1=0-1, i.e, 5 membered ring (n=0), 6 membered ring (n=1) and n2=1-4 carbons, i.e, 1, 2, 3, or 4 $CH_2$ moieties.

Experimental

In the present work, a β-cell survival-based high throughput screening approach was initially used to identify small molecules that protect β-cells against ER stress-induced apoptosis.

Figure 1B:
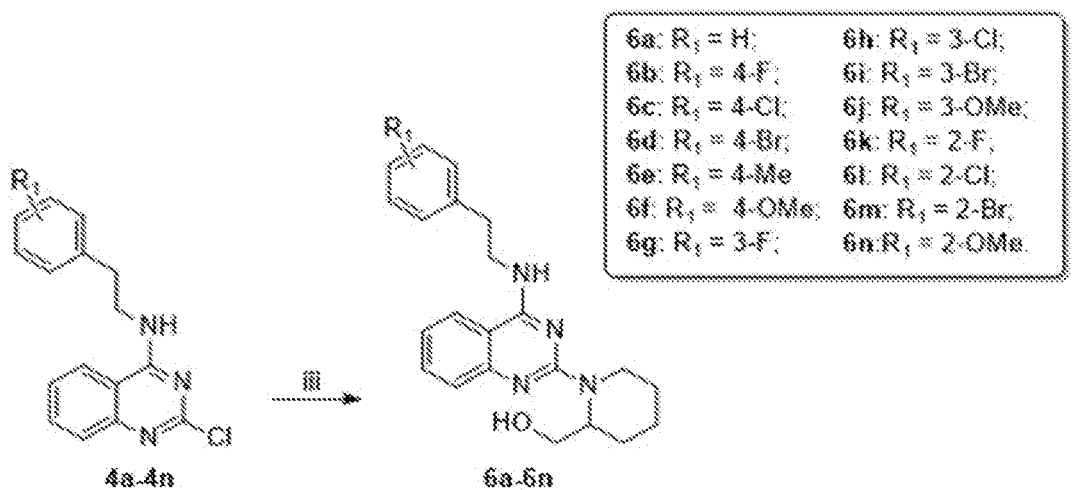
FIG. 1B shows schemes for the synthesis of 2,4-diaminoquinazoline derivatives 6a-6n and 7a-7d. Scheme 3: Synthesis of 2,4-diaminoquinazoline derivative compound 6a-n. Reagents and conditions used were: (reaction iii) 2-piperidinemethanol, DIEA, n-BuOH, 120° C., overnight, 50-85%. Scheme 4: Synthesis of 2,4-diaminoquinazoline derivative compound 7a-d. Reagents and conditions used were: (reaction ii) aryl amine, DIEA, n-BuOH, 40° C., 2 hrs, 65-85%.
Figure 1B:
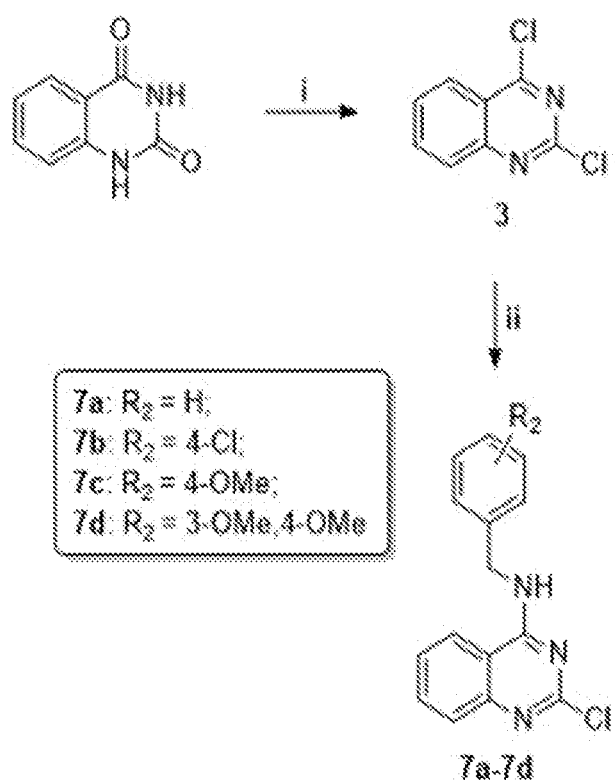
Figure 1C:
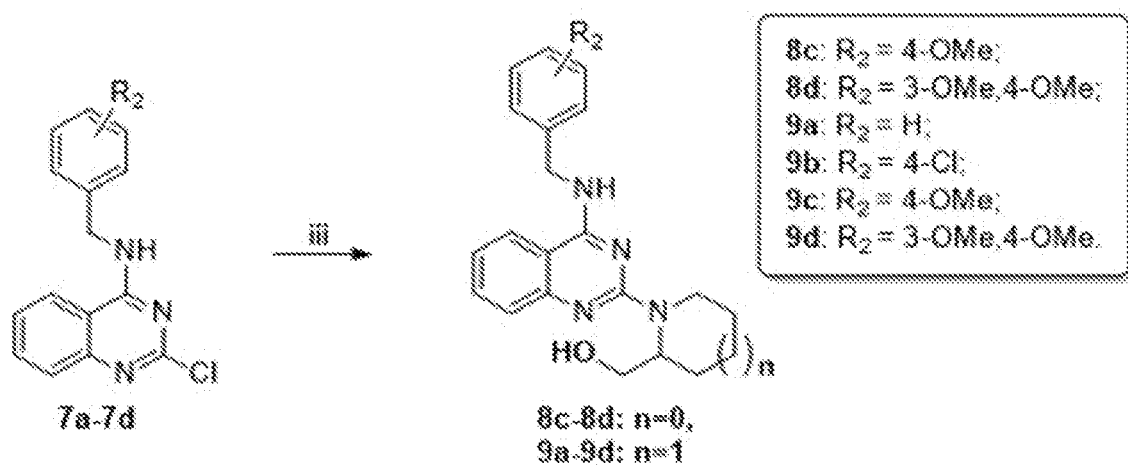
FIG. 1C shows a scheme for the synthesis of 2,4-diaminoquinazoline derivatives 8c-8d and 9a-9d. Scheme 5: Synthesis of 2,4-diaminoquinazoline derivative compound 8c-d and 9a-d. Reagents and conditions used were: (reaction iii) L-prolinol or 2-piperidinemethanol, DIEA, n-BuOH, 120° C., overnight, 50-85%.

FIGS. 1A-1C shows schemes for the synthesis of 2,4-diaminoquinazoline derivatives described herein. Scheme 1 shows synthesis of 2,4-diaminoquinazoline derivative compounds 4a-n. Scheme 2 shows synthesis of 2,4-diaminoquinazoline derivative compounds 5a-m. Scheme 3 shows synthesis of 2,4-diaminoquinazoline derivative compound 6a-n. Scheme 4 shows synthesis of 2,4-diaminoquinazoline derivative compound 7a-d. Scheme 5 shows synthesis of 2,4-diaminoquinazoline derivative compound 8c-d and 9a-d.

Using a rat INS-1 β-cell assay for β-cell-protective activity against ER stress, the small molecule compound (1-(4-(phenethylamino)quinazolin-2-yl)pyrrolidin-2-yl)methanol (5a), a 2,4-diaminoquinazoline compound, was discovered to be β-cell-protective against ER stress.

Although 5a is structurally novel, it has relatively weak activity on β-cell-protection (the maximum activity is 54.4% with an $EC_{50}$ value at 0.48±0.19 µM) which prompted further study into the β-cell-protection properties of this novel class of compounds. A structure-activity-relationship (SAR) study was thus conducted to improve the weak potency of lead compound 5a. Newly synthesized or commercially available compounds were tested for their β-cell-protective activity against ER stress in rat INS-1 β-cells. Treatment of INS-1 β-cells with tunicamycin (Tm), a potent ER stress inducer that inhibits N-linked glycosylation of proteins and causes the accumulation of misfolded proteins, significantly reduced cell viability at 72 h compared with DMSO-treated cells, as measured by an intracellular ATP level-based cell viability assay. The maximum activities and the concentrations that reach half-maximal activity ($EC_{50}$) of the compounds were evaluated by the degree of increase in viability of INS-1 cells co-treated with the compounds in the presence of Tm compared with Tm treatment alone. Maximum activity value in the tables is reported as % rescue from Tm (0.1 µg/mL)-induced reduction of cell viability. The values for Tm treatment alone and control (DMSO, without Tm) treatment are designated as 0% and 100%, respectively in all tables. $EC_{50}$ values (the concentrations that reach half-maximal activity) for INS-1 cell viability were calculated with GraphPad Prism from the data of ten 2-fold serial titration points in all tables. All experiments were performed in triplicate in all tables.

The initial focus was to create a series of 2,4-diaminoquinazoline derivatives incorporating a 2-(hydroxymethyl) pyrrolidin-1-yl group at the C-2 position of a quinazoline ring. (Chemical structure II, Table 1).

TABLE 1

Derivatives of chemical structure II: Activity of compounds 5a-5m on the survival of INS-1 cells treated with Tm.

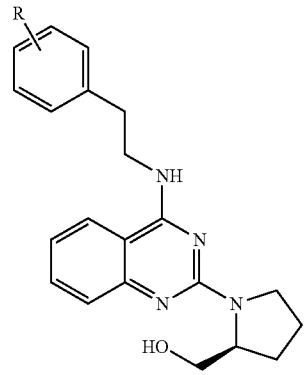

II

| Compd | R | Maximum activity[a] | $EC_{50}$ (µM)[b] |
|---|---|---|---|
| 5a | H | 54.4% | 0.48 ± 0.19 |
| 5b | 4-F | 56.2% | 2.13 ± 0.41 |
| 5c | 4-Cl | 57.3% | 0.51 ± 0.09 |
| 5d | 4-Br | 44.1% | 0.65 ± 0.16 |
| 5e | 4-$CH_3$ | 34.2% | 0.66 ± 0.21 |
| 5f | 3-F | 51.3% | 1.15 ± 0.19 |
| 5g | 3-Cl | 51.5% | 1.05 ± 0.18 |
| 5h | 3-Br | 53.2% | 0.78 ± 0.24 |
| 5i | 3-OMe | 54.9% | 1.51 ± 0.13 |
| 5j | 2-F | 52.5% | 1.70 ± 0.23 |
| 5k | 2-Cl | 50.6% | 1.44 ± 0.27 |
| 5l | 2-Br | 39.0% | 1.88 ± 0.32 |
| 5m | 2-OMe | 56.6% | 3.56 ± 0.15 |

The derivatives of the phenethylamine moieties substituted at para, meta, and ortho positions exhibited maximum activities ranging from ~34.2% to 57.3% as opposed to that as 100% in the absence of Tm, with no position being conferred to be more potent. However, more derivatives substituted at para position, including 5a, 5c, 5d and 5e, appeared to exhibit lower $EC_{50}$s at approximately 0.5 µM than derivatives substituted at meta and ortho positions.

We then investigated the structure-activity relationship between a five member ring and six membered ring by substituting 2-(hydroxymethyl)piperidin-1-yl at C-2 position of quinazoline (Chemical structure III, Table 2). Compared to the 2-(hydroxymethyl)pyrrolidin-1-yl derivatives, the maximum activities of the 2-(hydroxymethyl)piperidin-1-yl derivatives remained in a similar range except 6j. However, the $EC_{50}$s of these compounds improved over their 2-(hydroxymethyl)pyrrolidin-1-yl counterparts by ~2-3 fold (6a, 6c, 6d, 6e, 6h, 6l, and 6n versus 5a, 5c, 5d, 5e, 5g, 5k, and 5m respectively), with 6b improving by ~7 fold (6b versus 5b). 6j showed significantly improved maximum activity at 69.2% vs. its 2-(hydroxymethyl)pyrrolidin-1-yl counterpart 5i (54.9%), but its $EC_{50}$ also increased. Notably, among the 2-(hydroxymethyl)piperidin-1-yl derivatives, except bromo substitution which showed similar $EC_{50}$, the derivatives with para substitution, including 6a-f, exhibited relatively low $EC_{50}$s compared to ortho- or meta-substituted derivatives (6g-n). Taken together, this series of SAR studies indicates the 2-(hydroxymethyl)piperidin-1-yl moiety to be more favorable than its 2-(hydroxymethyl)pyrrolidin-1-yl counterpart in β cell protection against ER stress.

TABLE 2

Derivatives of chemical structure III: Activity of compounds 6a-6n on the survival of INS-1 cells treated with Tm.

III

| Compd | R | Maximum activity | $EC_{50}$ (μM) |
|---|---|---|---|
| 6a | H | 55.7% | 0.36 ± 0.21 |
| 6b | 4-F | 47.5% | 0.31 ± 0.26 |
| 6c | 4-Cl | 57.6% | 0.17 ± 0.05 |
| 6d | 4-Br | 52.8% | 0.34 ± 0.09 |
| 6e | 4-CH₃ | 33.6% | 0.14 ± 0.04 |
| 6f | 4-OMe | 58.6% | 0.31 ± 0.12 |
| 6g | 3-F | 57.3% | 1.88 ± 0.18 |
| 6h | 3-Cl | 46.2% | 0.79 ± 0.30 |
| 6i | 3-Br | 51.7% | 0.77 ± 0.40 |
| 6j | 3-OMe | 69.2% | 2.59 ± 0.31 |
| 6k | 2-F | 60.3% | 1.46 ± 0.46 |
| 6l | 2-Cl | 51.4% | 0.47 ± 0.45 |
| 6m | 2-Br | 44.2% | 1.41 ± 0.31 |
| 6n | 2-OMe | 46.9% | 1.60 ± 0.15 |

Figure 2:
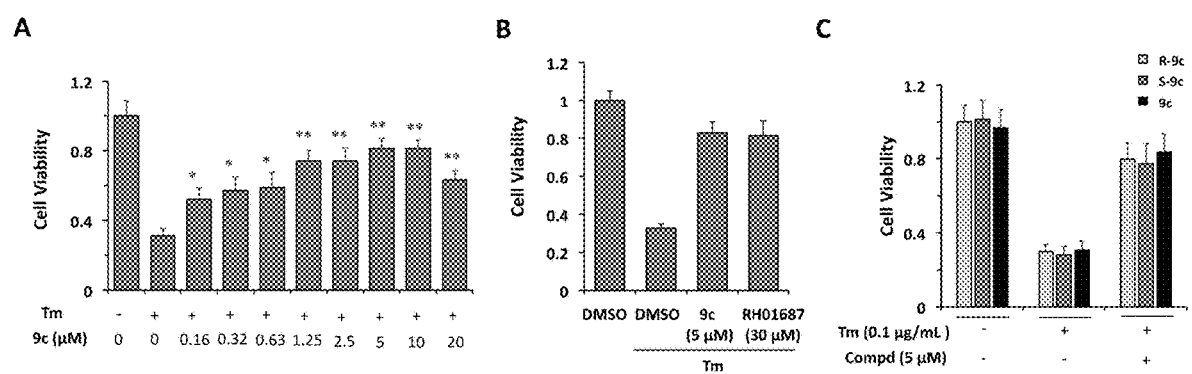
FIG. 2 shows the protective effects of 9c and its chiral forms on the viability of INS-1 cells after Tm treatments. (A) INS-1 cells were treated with or without Tm (0.1 μg/mL) in the presence of 9c at the indicated concentrations or DMSO for 72 h. (B) INS-1 cells were treated with 9c (5 μM), RH01687 (30 μM), or DMSO in the presence of Tm (0.1 μg/mL), or with DMSO in the absence of Tm, for 72 h. 5 μM of 9c and 30 μM of RH01687 were used as each at its chosen concentration respectively exhibited the maximum protective activity in INS-1 cells based on dose-dependent curves. (C) INS-1 cells were treated with or without Tm (0.1 μg/mL) in the presence of compounds (5 μM) or DMSO for 72 h. The cell viability was determined using the CellTiter-Glo assay, and was normalized as 1 for DMSO alone (in all figures unless specified). The results are the means of 3 replicate wells and are representative of 3 independent experiments. Bars indicate SD. **P<0.01 compared with Tm alone. DMSO concentration in all conditions (in all figures unless specified) is 0.1%.
Figure 9:
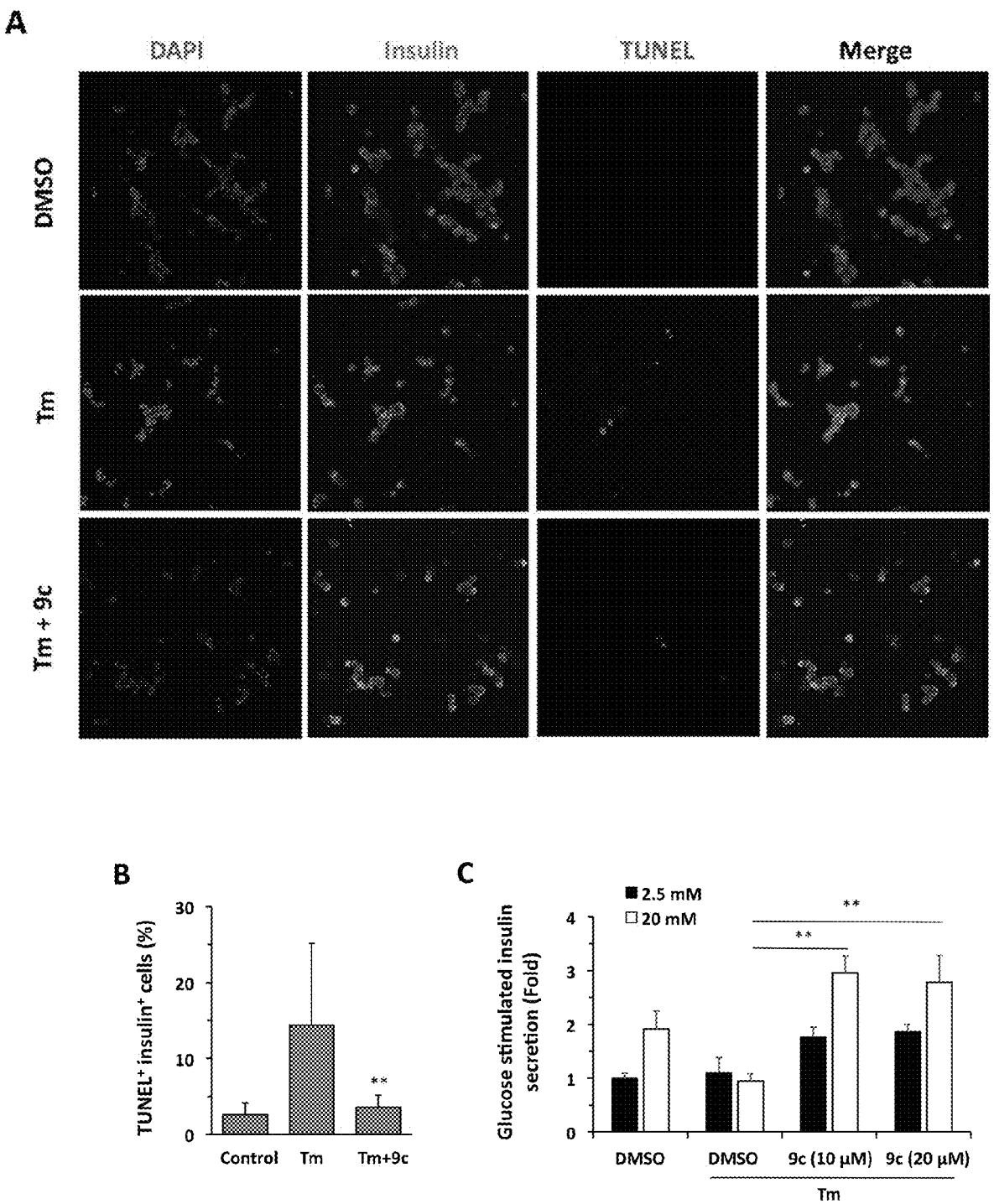
FIG. 9 shows that compound 9c protects human β cells against Tm-induced ER stress. (A) TUNEL staining of human β cells. Primary human islets were treated with 1 μg/mL of Tm with or without compound 9c (10 μM) for 48 h before TUNEL staining. Anti-insulin antibody was used to mark insulin-positive β cells, and DAPI was used as a nuclear marker. Magnification is 40×. (B) Quantification of TUNEL staining from 10 fields of images. P<0.01 compared with Tm treatment alone. (C) Insulin secretion by human islets (50 of equal size) incubated with 2.5 mM or 20 mM glucose in the presence of Tm (1 μg/mL) and 9c. Secreted insulin was measured by ELISA after 48 h treatment. For A and B, the values have been normalized to total cellular protein. The baseline insulin secretion at 2.5 mM glucose was normalized as 1. P<0.01.

Next, we shifted the SAR study to the phenethylamine moiety (Chemical structure IV, Table 3). When the amine linker length was shortened from two carbons to one, most resulting benzylamine compounds exhibited similar potency and maximum activity to their phenethylamine counterparts (6a versus 9a, and 6c versus 9b) (Tables 2 and 3). However, for the 4-OCH₃ derivatives, a benzyl group (9c) significantly improved the maximum activity over its phenethylamine counterpart 6f (80.4% versus 58.6%), with an $EC_{50}$ in the sub-micromolar range (0.56 μM) (Tables 2 and 3 and FIG. 2A). However, a derivative substituted at both meta and para positions with OCH₃ moieties (9d) exhibited less favorable activity than 9c (Table 3). We also synthesized the 2-(hydroxymethyl)pyrrolidine counterparts of both 9c and 9d, and observed that 9c and 9d showed more favorable activities than their 2-(hydroxymethyl)pyrrolidine derivatives in maximum activity (80.4% vs 57.2% and 69.4% vs 44.9%, respectively) (Table 3). Overall, all the SAR studies established that 9c is a more potent β cell-protective compound against ER stress in this series. Compared to RH01687 (a compound known to be β cell-protective against ER stress, as shown in FIG. 2B, 9c exhibited similar maximum activity to that of RH01687 but at significantly lower concentration (5 μM for 9c vs. 30 μM for RH01687).

TABLE 3

Derivatives of chemical structure IV: Activity of compounds 8c-9d on the survival of INS-1 cells treated with Tm.

IV

| Compound | R | n* | Maximum activity | $EC_{50}$ (μM) |
|---|---|---|---|---|
| 8c | 4-OMe | 0 | 57.2% | 4.05 ± 0.13 |
| 8d | 3,4-diOMe | 0 | 44.9 % | 1.85 ± 0.39 |
| 9a | H | 1 | 56.4 % | 0.23 ± 0.07 |
| 9b | 4-Cl | 1 | 54.7 % | 0.21 ± 0.08 |
| 9c | 4-OMe | 1 | 80.4 % | 0.56 ± 0.18 |
| 9d | 3,4-diOme | 1 | 69.4 % | 3.64 ± 0.38 |

*: Ring is 5-membered when n=0 and is 6-membered when n=1.

To explore whether the chirality of 9c influenced its potency, the R (R-9c) and S (S-9c) isomers of compound 9c were synthesized. As shown in FIG. 2C, both R-9c, and S-9c compounds exhibited similar $EC_{50}$s and maximum activities in increasing the viability of INS-1 cells after Tm treatment. We therefore chose racemic 9c for further characterization of its mechanism of action in promoting β cell survival and function against ER stress.

Figure 3:
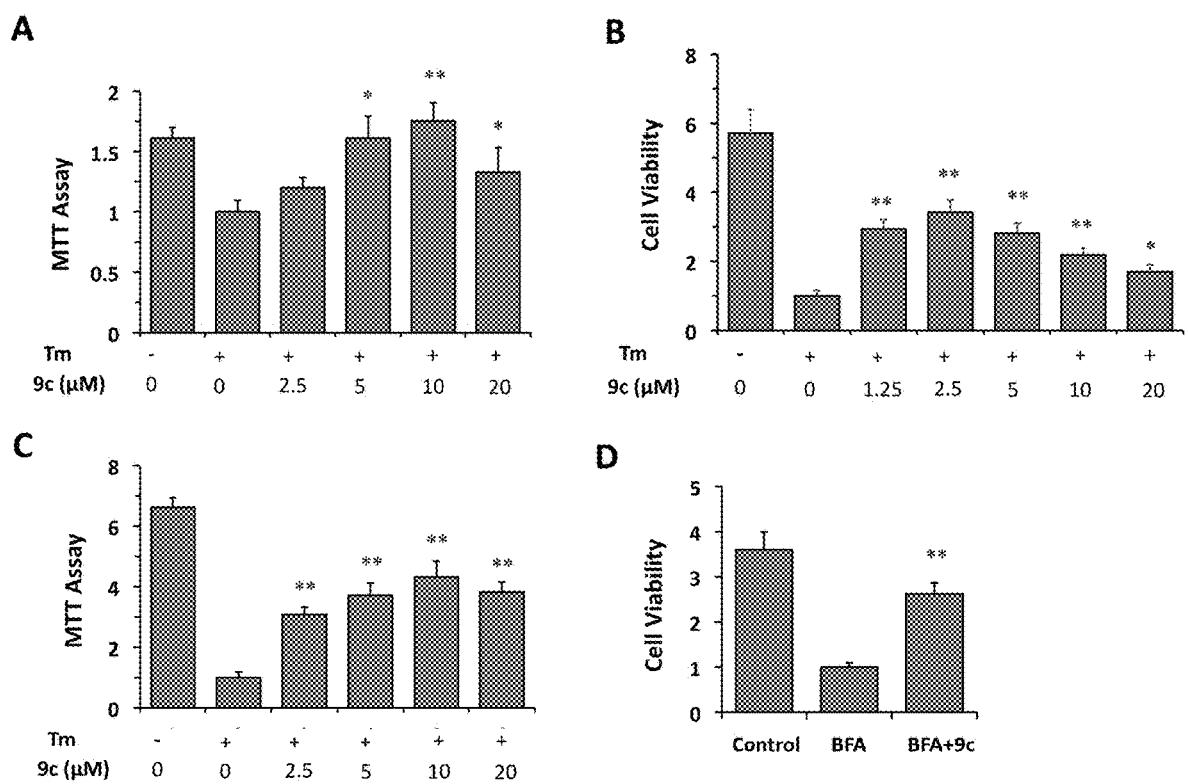
FIG. 3 shows that compound 9c increases the viability of β cells against ER stress. (A) INS-1 cells were treated with or without Tm (0.1 μg/mL) in the presence of 9c or DMSO for 72 h. The cell viability was determined using MTT. (B, C) βTC6 cells were treated with or without Tm (0.25 μg/mL) in the presence of 9c or DMSO for 72 h. The cell viability was determined using CellTiter-Glo assay (B) or MTT (C). (D) INS-1 cells were treated with or without BFA (0.2 μg/mL) in the presence of 9c (20 μM) or DMSO for 72 h. The cell viability was determined by CellTiter-Glo. The results in all panels are the means of 3 replicate wells and are representative of 3 independent experiments. *P<0.05 and **P<0.01 compared with Tm or BFA treated alone. Bars indicate SD.

To rule out the possibility of an ATP-specific (rather than viability) effect of the compounds, we used the MTT assay, which measures the activity of NAD(P)H-dependent cellular oxidoreductase enzymes, as an orthogonal method to measure cell viability. As shown in FIG. 3A, Tm treatment reduced the MTT reading in INS-1 cells compared to that of DMSO treatment, and co-treatment with 9c resulted in an increase in viability of INS-1 cells. To confirm that the protective effect of 9c on β cells is not INS-1 cell-specific, another β cell line, βTC6, was used. As expected, Tm induced a reduction in viability in βTC6 cells, and co-treatment with 9c rescued the viability of βTC6 cells in a dose-dependent manner, as assessed by both intracellular ATP level and activity of NAD(P)H-dependent cellular oxidoreductase enzymes (FIGS. 3B and 3C). To determine whether the protective effect of 9c on β cells is specific to Tm-induced stress, we used another ER stressor, BFA, which inhibits a key guanine nucleotide exchange factor essential for the transport of proteins from the ER to the Golgi, to treat INS-1 cells. Indeed, compound 9c also protected INS-1 cells against BFA (FIG. 3D). All these results indicate that compound 9c protects β cell survival against ER stress.

Figure 4:
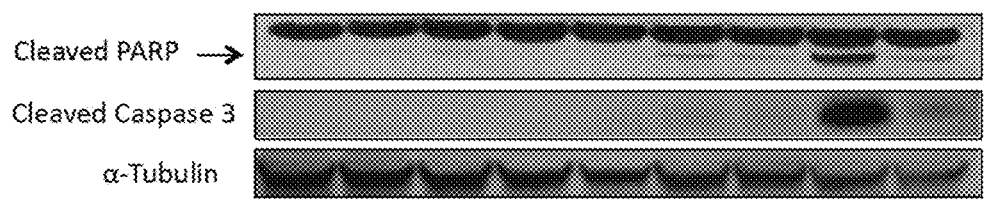
FIG. 4 shows that compound 9c protects INS-1 cells against Tm-induced apoptosis. (A) INS-1 cells were treated with or without Tm (0.1 μg/mL) in the presence of 9c (20 μM) or DMSO for the indicated times. Cleaved caspase-3 and PARP were determined by Western blotting. A-Tubulin was used as a loading control. The data shown are representative of 3 independent experiments. (B) INS-1 cells were treated with or without Tm (0.1 μg/mL) in the presence of 9c (20 μM) or DMSO for 24 h, and live-cell phase-contrast images were acquired (magnification 10×).
Figure 4:
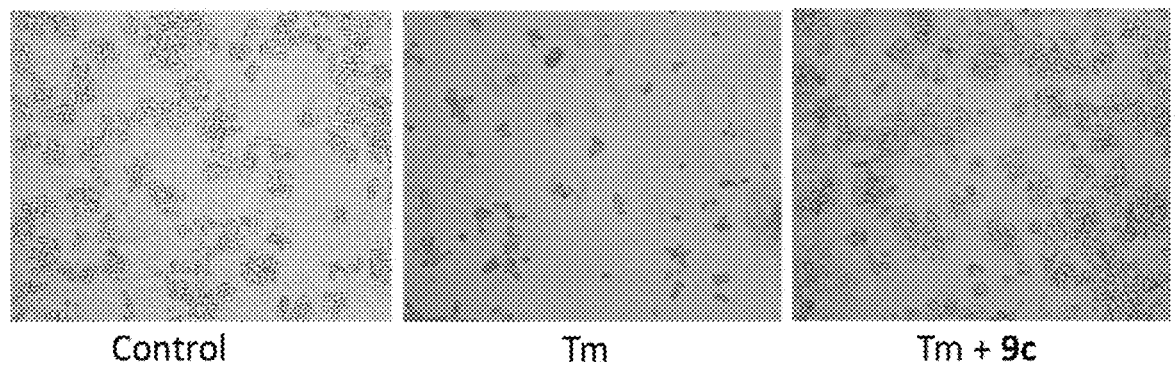

To determine whether the increase in cell viability following treatment with 9c was caused by a suppression of apoptotic cell death, levels of cleaved caspase-3 and cleaved PARP were assessed by Western blotting. Caspase-3, a member of executioner caspases, plays essential roles in initiating apoptotic signaling and executing the final stages of cell death as it is responsible for the proteolytic cleavage of many key proteins, such as the nuclear enzyme poly (ADP-ribose) polymerase (PARP) which is a family of proteins involved in a number of cellular processes involving DNA repair and cell death. Under normal condition, caspase 3 exists as inactive proenzyme. However, upon severe ER stress, caspase 3 undergoes proteolytic cleavage to produce two subunits that dimerize to form the active enzyme, which in turns cleaves PARP. Hence, appearance of the cleaved forms of both caspase-3 and PARP is an indication of apoptosis. Tm treatment for 24 h significantly induced both cleaved caspase-3 and cleaved PARP protein levels in INS-1 cells (FIG. 4A). However, 9c co-treatment significantly reversed Tm-induced cleavage of both caspase-3 and PARP (FIG. 4A). These results demonstrate that 9c inhibits Tm-induced activation of caspase 3 and apoptosis in INS-1 cells. Consistent with this, significantly more viable cells were observed with Tm and 9c co-treatment than with Tm alone (FIG. 4B).

Figure 5:
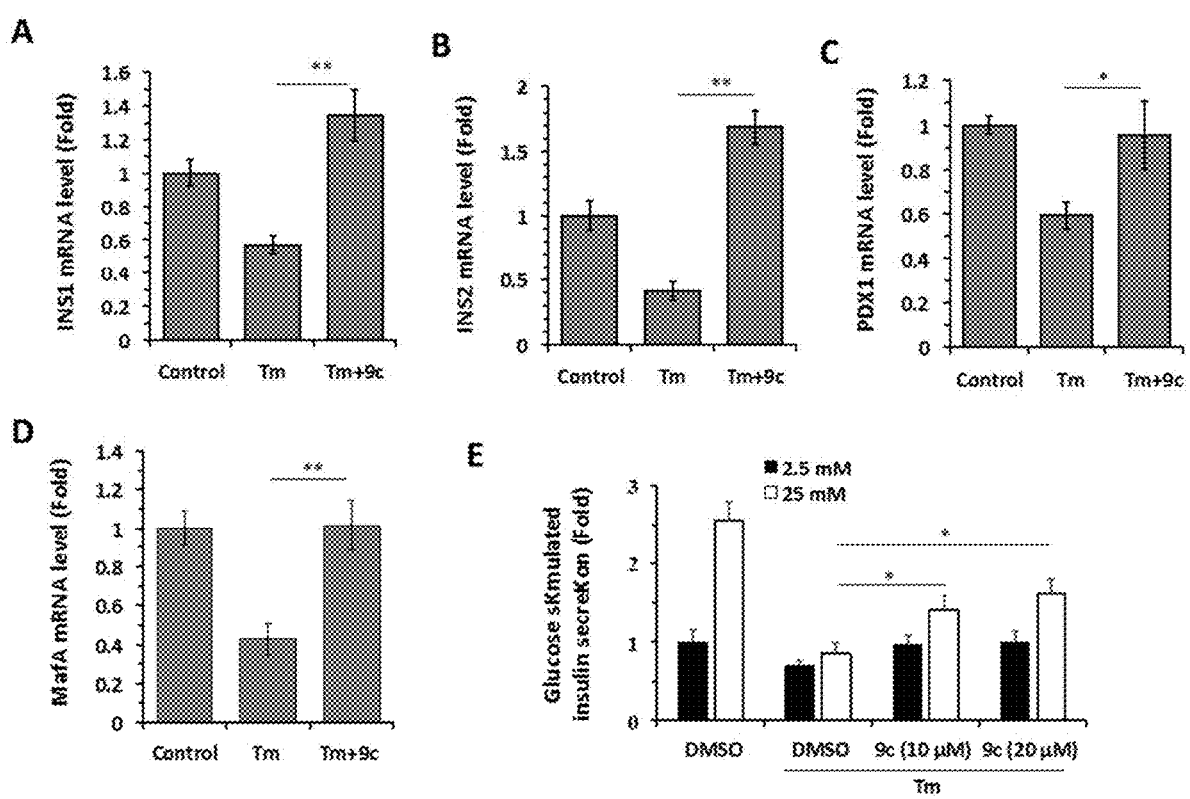
FIG. 5 shows that compound 9c reverses Tm-suppressed β cell function. (A-D) INS-1 cells were treated with or without Tm (0.1 μg/mL) in the presence of 9c (20 μM) or DMSO for 24 h. The mRNA levels of INS1 (A), INS2 (B), PDX1 (C), and MafA (D), were analyzed by qRT-PCR. The results are the means of 3 replicate wells and are representative of 3 independent experiments. *P<0.05 and **P<0.01. Bars indicate SD. (E) Insulin secretion by INS-1 cells incubated with 2.5 mM and 25 mM glucose in the presence of Tm (0.1 μg/mL) and 9c. Secreted insulin was measured by ELISA after 24 h treatment. *P<0.05. The amount of insulin secreted in response to 2.5 mM glucose in the absence of Tm was set to 1.0.

ER stress also impairs the most important function of β cells: the biosynthesis and secretion of insulin. Multiple steps of insulin synthesis and secretion are impaired under ER stress; they include insulin gene transcription, insulin mRNA stability, protein translation, and the insulin protein secretory process. First, we examined whether compound 9c could rescue Tm-suppressed mRNA levels of insulin genes. As expected, Tm treatment of INS-1 cells decreased the mRNA levels of both insulin genes, INS1 and INS2, but this reduction was completely rescued by 9c (FIGS. 5A and B). Second, we examined whether compound 9c affects the expression of β cell transcription factors PDX1 and MafA, which control β cell identity and the expression of insulin genes. Chronic exposure to supraphysiologic concentrations of glucose and its associated ER stress cause the down-regulation of expression of PDX1 and MafA. Consistent with this notion, Tm decreased the levels of PDX1 and MafA mRNA expression levels in INS-1 cells. Co-treatment with 9c almost completely reversed this decrease to normal levels (FIGS. 5C and D). Next, we explored whether compound 9c re-establishes Tm-impaired glucose-stimulated insulin secretion (GSIS). As shown in FIG. 5E, Tm treatment abolished the insulin secretion caused by high concentration of glucose treatment (25 mM) in INS-1 cells. Addition of 9c significantly rescued the GSIS in Tm-treated cells. Taken together, these data demonstrate that 9c restores ER stress-impaired β cell survival and function.

Figure 6:
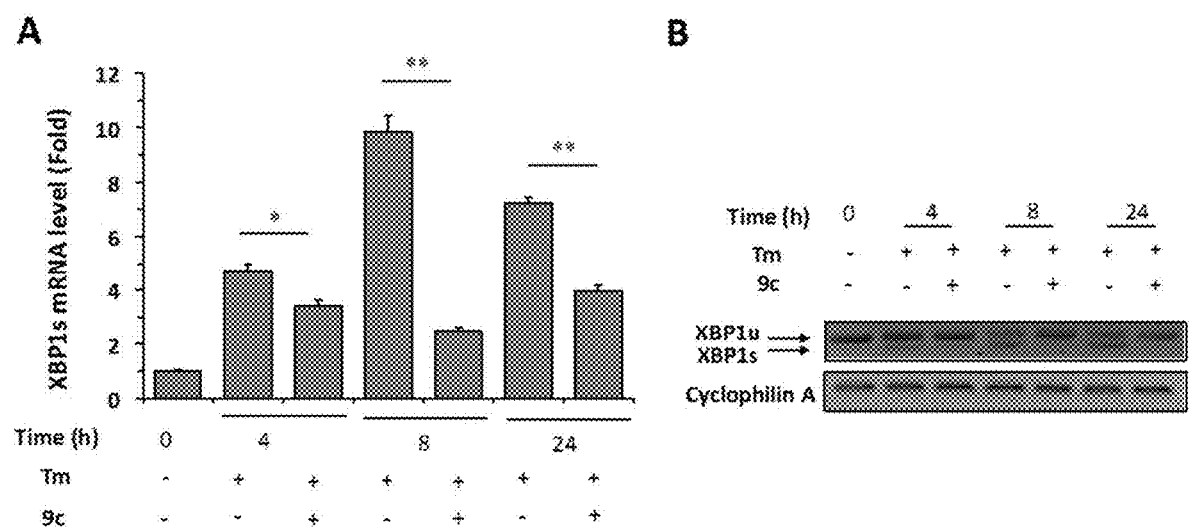
FIG. 6 shows that compound 9c decreases XBP1s mRNA levels induced by Tm. INS-1 cells were treated with or without Tm (0.1 μg/mL) in the presence of 9c (20 μM) or DMSO for the indicated times. (A) XBP1s mRNA levels were analyzed by qRT-PCR. The results are expressed as the fold-increase over mRNA levels in untreated control cells and are the means of 3 replicate wells and representative of 3 independent experiments. *P<0.05 and **P<0.01. Bars indicate SD. (B) XBP1 mRNA levels were analyzed by RT-PCR and the products were resolved by agarose gel electrophoresis. The full-length (unspliced, XBP1u) and spliced (XBP1s) forms of XBP1 mRNA are indicated. Cyclophilin A mRNA was used as an internal control. The data shown are representative of 3 independent experiments.

Next, we investigated the mechanism by which 9c protects β cells against ER stress. In response to ER stress, all three branches of the UPR, IRE1α, PERK and ATF6, are activated to either restore cellular homeostasis/survival or lead to cell death, depending on the severity of ER stress. First, we asked whether 9c affects the activation of IRE1α in β cells under ER stress. Activated IRE1α cleaves X-box binding protein-1 (XBP1) mRNA to generate a spliced form (XBP1s) that is translated into a potent transcription factor which controls expression of UPR genes encoding factors involved in ER protein folding and degradation. We therefore determined the effect of 9c on IRE1α-mediated XBP1 splicing in INS-1 cells in the presence of Tm. As shown in FIG. 6A, INS-1 cells treated with Tm exhibited an increase in XBP1s mRNA, and this increase was suppressed by 9c co-treatment, as measured by qRT-PCT using XBP1 splicing-specific primers. Likewise, electrophoretic separation of spliced and unspliced forms of XBP1 after RT-PCR amplification of total XBP1 mRNA revealed that 9c inhibits the Tm-induced generation of XBP1s mRNA (FIG. 6B). These results indicate that 9c inhibits the activation of the IRE1α-XBP1 pathway of the UPR.

Figure 7:
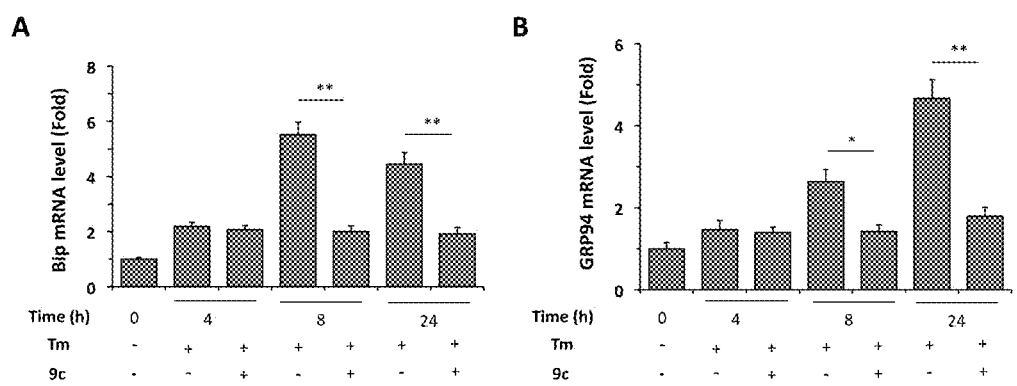
FIG. 7 shows that compound 9c inhibits Tm-induced Bip and GRP94 expression in INS-1 cells. INS-1 cells were treated with or without Tm (0.1 μg/mL) in the presence of 9c (20 μM) or DMSO for the indicated times. Bip (A) and GRP94 (B) mRNA levels were analyzed by qRT-PCR. The results are expressed as the fold-increase over mRNA levels in untreated control cells and are the means of 3 replicate wells and representative of 3 independent experiments. *P<0.05 and **P<0.01.

We then asked whether 9c affects the activation of ATF6 in β cells under ER stress. Activated ATF6 acts as a homodimer or as an ATF6-XBP1s heterodimer to control the up-regulation of select UPR target genes including the chaperone proteins BiP and GRP94. We evaluated the effect of 9c on the mRNA levels of chaperones Bip and GRP94 in β cells in the presence of Tm. As expected, we found that both Bip and GRP94 mRNAs were up-regulated in INS-1 cells treated with Tm. These increases were almost completely suppressed by 9c co-treatment (FIGS. 7A and B).

Figure 8:
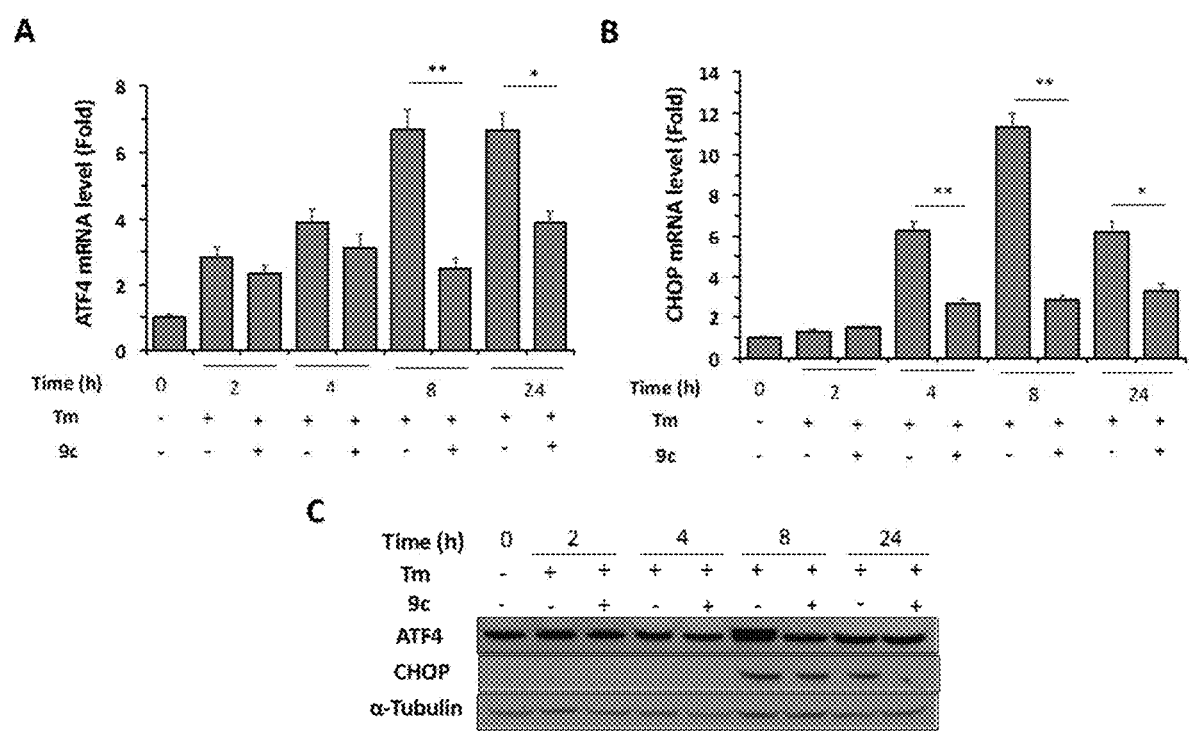
FIG. 8 shows that compound 9c inhibits Tm-induced ATF4 and CHOP up-regulation in INS-1 cells. (A, B) INS-1 cells were treated with or without Tm (0.1 μg/mL) in the presence of 9c (20 μM) or DMSO for the indicated times. ATF4 (A) and CHOP (B) mRNA levels were analyzed by qRT-PCR. The results are expressed as the fold-increase over mRNA levels in untreated control cells and are the means of 3 replicate wells and representative of 3 independent experiments. *P<0.05 and **P<0.01. Bar indicates SD. (C) INS-1 cells were treated with or without Tm (0.1 μg/mL) in the presence of 9c (20 μM) or DMSO for the indicated times. ATF4 and CHOP protein levels were determined by Western blotting. α-Tubulin was used as a loading control. The data shown are representative of 3 independent experiments.

We then determined the effect of 9c on the activation of the PERK pathway in β cells under ER stress. Activated PERK phosphorylates eukaryotic translation initiator factor 2a (eIF2α), which in turn attenuates general protein synthesis to relieve ER load. EIF2α phosphorylation also allows the selective translation of ATF4 mRNA, which encodes a transcription factor that induces the expression of the pro-apoptotic gene C/EBP-homologous protein (CHOP). Thus, we used ATF4 and CHOP expression levels as markers of PERK pathway activation. Tm treatment of INS-1 cells significantly increased the mRNA levels of both ATF4 and CHOP, whereas co-treatment with 9c resulted in a decrease in both their levels (FIGS. 8A and B). Tm treatment also increased the ATF4 protein level with the peak time at 8 h and CHOP protein level starting at 8 h (FIG. 8C). Consistent with its effects on ATF4 and CHOP mRNA transcription, 9c co-treatment also decreased ATF4 and CHOP protein levels in Tm-treated INS-1 cells (FIG. 8C). Together, our results that 9c inhibited the ER stress-mediated activation of all three UPR pathways indicate that 9c protects β cell survival by alleviating ER stress.

Finally, we investigated whether 9c exhibits similar protective effects on primary human islet β cells to exclude the possibility that our findings are merely unique to rodent β cells. Rodent models of mammalian β cell biology have been invaluable tools for the understanding of β cell physiology and diabetes pathogenesis; however, human and rodent β cells differ in fundamental ways. For example, the pancreatic islet architecture is markedly different between humans and rodents. In rodents, the islets are more organized, comprising a large core of β cells (representing ~80% of islet cells) enveloped by a layer of a cells and other endocrine cells. However, in humans, β cells account for only ~50% of islet cells and are scattered throughout the islet. Rodent β cells also show significant regenerative capacity that human β cells lack. Moreover, among hundreds of manipulations reported to prevent or cure T1D in the NOD diabetic mouse model, very few demonstrate a limited efficacy in T1D patients. Therefore, agents that function well in rodent systems need to be confirmed in human systems. We utilized primary human islets to evaluate whether 9c protects β cell survival and function impaired by ER stress. Another advantage of human islets is that they are primary cells and, therefore, share more authentic properties with β cells than immortalized cell lines.

Figure 10:
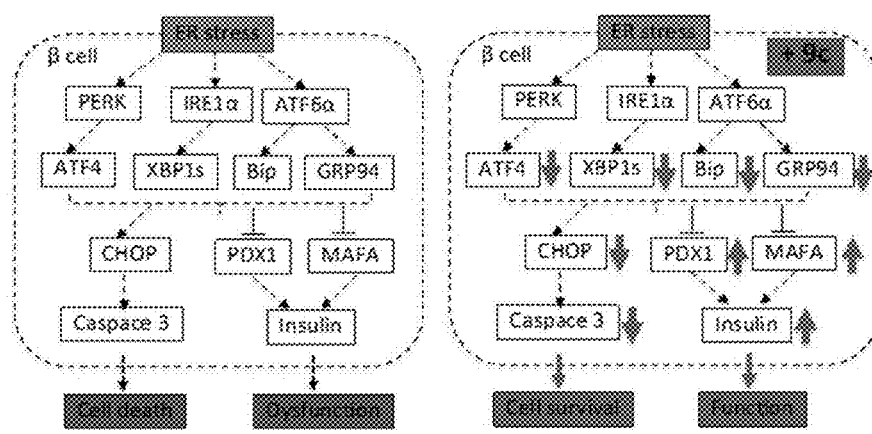
FIG. 10 shows a proposed model of signaling pathways involved in 9c-mediated β cell-protective effects against ER stress. ER stress induces activation of three branches of UPR (PERK, IRE1α, and ATF6), leading to up-regulation of ATF4, XBP1s, Bip, GRP4, CHOP and eventual activation caspase 3 and cell apoptosis, while diminishing the expression of PDX1, MAFA and insulin genes, leading to β cell dysfunction. Compound 9c protects β cell against ER stress-mediated dysfunction and death by down-regulating ATF4, XBP1s, Bip, GRP94, CHOP, and caspase 3 and up-regulating PDX1, MAFA and insulin genes.

We determined whether 9c suppresses the apoptosis of primary human β cells induced by Tm treatment as assessed by TUNEL, which detects fragmentation of DNA, a marker of apoptotic cell death. As expected, Tm treatment markedly increased TUNEL staining in insulin[+] cells (15% TUNEL[+]

insulin+ cells compared to 2.5% with DMSO) (FIGS. 9A and B). Compound 9c co-treatment significantly decreased the percentage of TUNEL+ insulin+ cells to 3.5% (FIGS. 9A and B). Next, we investigated whether 9c restored the Tm-induced insulin secretion defect. Tm treatment markedly diminished the high glucose-stimulated increase in insulin secretion, but the addition of 9c significantly reversed this effect and restored the Tm-impaired GSIS (FIG. 9C). These data indicate that 9c is equally effective for the protection of human β cells as for rodent β cells. FIG. 10 shows a proposed model of signaling pathways involved in 9c-mediated β cell-protective effects against ER stress. ER stress induces activation of three branches of UPR (PERK, IRE1α, and ATF6), leading to up-regulation of ATF4, XBP1s, Bip, GRP4, CHOP and eventual activation caspase 3 and cell apoptosis, while diminishing the expression of PDX1, MAFA and insulin genes, leading to β cell dysfunction. Compound 9c protects β cell against ER stress-mediated dysfunction and death by down-regulating ATF4, XBP1s, Bip, GRP94, CHOP, and caspase 3 and up-regulating PDX1, MAFA and insulin genes.

Methods

Chemistry

The reagents and solvents were purchased and were used without further purification. All compounds were purified by flash column chromatography on Sorbent Technologies silica gel, 60 Å (63-200 mesh). TLC was done on SAI F254 precoated silica gel plates (250 μm layer thickness). $^1$H NMR and $^{13}$C NMR spectra were recorded on a Bruker AVANCE III 400 MHz spectrometer using tetramethylsilane as an internal reference. ESI-MS spectra were obtained on a Krats MS 80 mass spectrometer. The purity of all tested compounds was at least above 95% as determined by HPLC.

General procedure and characterization of compounds 3, 4a-n, 5a-m, 6a-n, 7a-d, 8c-9d.

3 was obtained by adding dimethylaniline (640.5 mg, 5.26 mmol) to a mixture of benzoylenurea (800 mg, 4.93 mmol) in POCl$_3$ (10 ml) at room temperature. The reaction mixture was stirred at 120° C. for 24 h. The reaction mixture was quenched with ice-cold water. The reddish solid, compound 3, was precipitated, vacuum filtered, and then washed with hexane and dried under vacuum. It was used without further purification (672.3 mg, 68.6%). $^1$H NMR (400 MHz, CDCl$_3$) δ 8.27 (ddd, J=8.4, 2.0, 0.8 Hz, 1H), 8.03-8.00 (m, 2H), 7.77-7.73 (m, 1H). $^{13}$C NMR (100 MHz, CDCl$_3$) δ 164.0, 155.1, 152.4, 136.2, 129.3, 128.0, 126.1, 122.4. LC-MS (ESI, formic) m/z 199.0 [M+H]$^+$.

4a was obtained by taking a solution of compound 3 (100 mg, 0.56 mmol) in n-BuOH (3 mL) which was then treated with DIEA (215.9 mg, 1.67 mmol) and phenethylamine (67.9 mg, 0.56 mmol). The reaction mixture was stirred for 2 h at 40° C. and the solvent was evaporated. The residue was extracted with methylene chloride (30 mL, 3 times) and water. The organic layer was dried over Na$_2$SO$_4$ and evaporated. Compound 4a was purified from this crude material by column chromatography (silicagel, n-hexane/EtOAc=3:1) (117.4 mg, 73.9%). $^1$H NMR (400 MHz, CDCl$_3$) δ 7.77-7.74 (dd, J=8.4, 1.2 Hz, 1H), 7.72 (ddd, J=8.4, 6.8, 1.2 Hz, 1H), 7.49 (d, J=7.6 Hz, 1H), 7.40 (ddd, J=8.4, 6.8, 1.6 Hz, 1H), 7.37-7.33 (m, 2H), 7.29-7.25 (m, 3H), 5.94 (br s, 1H), 3.95 (q, J=6.8, 5.6 Hz, 2H), 3.03 (t, J=6.8 Hz, 2H). $^{13}$C NMR (100 MHz, CDCl$_3$) δ 160.8, 157.8, 150.8, 138.5, 133.5, 128.9, 127.9, 126.8, 126.2, 120.5, 113.3, 42.5, 35.0. LC-MS (ESI, formic) m/z 284.1 [M+H]$^+$.

5a was obtained by taking a solution of 4a (50 mg, 0.176 mmol) in n-BuOH (2 mL) and was then treated with DIEA (68.3 mg, 0.529 mmol) and L-prolinol (53.5 mg, 0.529 mmol). The resulting mixture was stirred overnight at 120° C. and the solvent was evaporated. The residue was extracted with methylene chloride (20 mL, 3 times) and water. The organic layer was dried over Na$_2$SO$_4$ and evaporated. Compound 5a was purified from this crude material by column chromatography (silicagel, CH$_2$Cl$_2$:MeOH:triethylamine=10:1:0.1) (39.6 mg, 64.6%). purity (97.96%); $^1$H NMR (400 MHz, CDCl$_3$) δ 7.48 (ddd, J=8.4, 6.8, 1.2 Hz, 1H), 7.40 (t, J=8.8 Hz, 2H), 7.35-7.31 (m, 2H), 7.27-7.23 (m, 3H), 7.01 (ddd, J=8.4, 7.2, 1.2 Hz, 1H), 5.97 (br s, 1H), 4.40-4.35 (m, 1H), 3.99-3.93 (m, 1H), 3.88-3.78 (m, 3H), 3.72-3.63 (m, 2H), 3.02 (t, J=7.2 Hz, 2H), 2.20-2.12 (m, 1H), 1.99-1.83 (m, 2H), 1.71-1.63 (m, 1H). $^{13}$C NMR (100 MHz, CDCl$_3$) δ 159.6, 158.4, 139.1, 132.9, 128.9, 128.7, 126.6, 124.5, 121.1, 120.8, 110.2, 68.7, 61.1, 48.5, 42.5, 35.3, 30.0, 24.1. HRMS calculated for C$_{21}$H$_{25}$N$_4$O ([M+H]$^+$) m/z 349.2028, found m/z 349.2029; mp 171.8-175.5° C.

6a was obtained by taking a solution of 4a (50 mg, 0.176 mmol) in n-BuOH (2 mL) and was then treated with DIEA (68.3 mg, 0.529 mmol) and 2-piperidinemethanol (60.9 mg, 0.529 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 6a was purified from this crude material by column chromatography (silicagel, CH$_2$Cl$_2$:MeOH:triethylamine=10:1:0.1) (43.3 mg, 67.9%). purity (99.90%); $^1$H NMR (400 MHz, CDCl$_3$) δ 7.53 (d, J=8.0 Hz, 1H), 7.48-7.36 (m, 4H), 7.11 (d, J=8.4 Hz, 2H), 7.07-7.03 (m, 1H), 6.39 (br s, 1H), 4.99 (d, J=4.0 Hz, 1H), 4.77 (d, J=13.6 Hz, 1H), 4.09 (t, J=10.8, 10.4 Hz, 1H), 3.82-3.75 (m, 3H), 3.21-3.14 (m, 1H), 2.96 (t, J=7.2 Hz, 2H), 1.76-1.58 (m, 6H). $^{13}$C NMR (100 MHz, CDCl$_3$) δ 159.4, 138.0, 133.1, 131.8, 130.6, 122.1, 121.2, 120.5, 110.2, 53.9, 42.4, 40.0, 34.6, 29.7, 26.3, 25.2, 20.0. HRMS calcd for C$_{22}$H$_{27}$N$_4$O ([M+H]$^+$) m/z 363.2185, found m/z 363.2177; mp 159.0-161.1.

4b was obtained by taking a solution of compound 3 (100 mg, 0.56 mmol) in n-BuOH (3 mL) and was then treated with DIEA (215.9 mg, 1.67 mmol) and 4-fluorophenethylamine (77.9 mg, 0.56 mmol). The reaction mixture was stirred for 2 h at 40° C. and the solvent was evaporated. The residue was extracted with methylene chloride (20 mL, 3 times) and water. The organic layer was dried over Na$_2$SO$_4$ and evaporated. Compound 4b was purified from this crude material by column chromatography (silicagel, n-hexane/EtOAc=3:1) (114.3 mg, 67.6%). $^1$H NMR (400 MHz, CDCl$_3$) δ 7.76-7.70 (m, 2H), 7.52 (d, J=8.0 Hz, 1H), 7.42 (ddd, J=8.0, 6.4, 1.6 Hz, 1H), 7.23-7.18 (m, 2H), 7.04-6.99 (m, 2H), 5.99 (br s, 1H), 3.92 (q, J=7.0 Hz, 2H), 3.01 (t, J=7.0 Hz, 2H). $^{13}$C NMR (100 MHz, CDCl$_3$) δ 163.0, 160.8, 160.6, 157.8, 150.8, 133.5, 130.3, 130.2, 127.9, 126.3, 120.5, 115.8, 115.5, 113.2, 42.6, 34.3. LC-MS (ESI, formic) m/z 302.1 [M+H]$^+$.

5b was obtained by taking a solution of 4b (50 mg, 0.166 mmol) in n-BuOH (2 mL) then was treated with DIEA (64.2 mg, 0.497 mmol) and L-prolinol (50.3 mg, 0.497 mmol). The reaction mixture was stirred overnight at 120° C. and the solvent was evaporated. The residue was extracted with methylene chloride (30 mL, 3 times) and water. The organic layer was dried over Na$_2$SO$_4$ and evaporated. Compound 5b was purified from this crude material by column chromatography (silicagel, CH$_2$Cl$_2$:MeOH:triethylamine=10:1:0.1) (31.5 mg, 51.8%). purity (99.30%); $^1$H NMR (400 MHz, CDCl$_3$) δ 7.48 (ddd, J=8.4, 7.2, 1.2 Hz, 1H), 7.39 (t, J=7.2, 6.4 Hz, 2H), 7.20-7.17 (m, 2H), 7.03-6.98 (m, 3H), 5.92 (br s, 1H), 4.40-4.34 (m, 1H), 3.98-3.92 (m, 1H), 3.84-3.78 (m, 3H), 3.71-3.62 (m, 2H), 2.99 (t, J=7.2 Hz, 2H), 2.20-2.11 (m, 1H), 2.01-1.84 (m, 2H), 1.70-1.63 (m, 1H). $^{13}$C NMR (100 MHz, CDCl$_3$) δ 162.9, 160.5, 159.6, 158.5, 132.9, 130.3, 130.2, 121.1, 120.7, 115.6, 115.4, 110.2, 68.8, 61.1, 48.5, 42.6, 34.5, 29.9, 24.1. HRMS (FAB) calcd for C$_{21}$H$_{24}$FN$_4$O ([M+H]$^+$) m/z 367.1934, found m/z 367.1931.

6b was obtained by taking a solution of 4b (50 mg, 0.166 mmol) in n-BuOH (2 mL) then was treated with DIEA (64.2 mg, 0.497 mmol) and 2-piperidinemethanol (57.3 mg, 0.497 mmol). The reaction mixture was stirred overnight at 120° C. and the solvent was evaporated. The residue was extracted with methylene chloride (30 mL, 3 times) and water. The organic layer was dried over Na$_2$SO$_4$ and evaporated. Compound 6b was purified from this crude material by column chromatography (silicagel, CH$_2$Cl$_2$:MeOH:triethylamine=10:1:0.1) (37.4 mg, 59.2%). purity (97.70%); $^1$H NMR (400 MHz, CDCl$_3$) δ 7.49 (d, J=4.4 Hz, 2H), 7.37 (d, J=8.0 Hz, 1H), 7.22-7.18 (m, 2H), 7.07-6.99 (m, 3H), 5.95 (br s, 1H), 5.05-5.02 (m, 1H), 4.80 (d, J=13.6 Hz, 1H), 4.11 (t, J=10.8, 10.0 Hz, 1H), 3.84-3.77 (m, 3H), 3.22-3.16 (m, 1H), 2.99 (t, J=7.2, 6.8 Hz, 2H), 2.04-2.00 (m, 1H), 1.76-1.71 (m, 3H), 1.68-1.58 (m, 4H). $^{13}$C NMR (100 MHz, CDCl$_3$) δ 162.9, 159.5, 134.6, 132.9, 130.3, 130.2, 121.6, 120.7, 115.7, 115.4, 110.3, 63.9, 53.7, 42.6, 40.0, 34.4, 29.7, 26.4, 25.3, 20. HRMS calcd for C$_{22}$H$_{26}$FN$_4$O ([M+H]$^+$) m/z 381.2091, found m/z 381.2094; mp 147.1-149.5° C.

4c was obtained by taking a solution of compound 3 (100 mg, 0.56 mmol) in n-BuOH (3 mL) and then DIEA (215.9 mg, 1.67 mmol) and 4-chlorophenethylamine (87.1 mg, 0.56 mmol) were added. The reaction mixture was stirred for 2 hours at 40° C. and the solvent was evaporated. The residue was extracted with methylene chloride (30 mL, 3 times) and water. The organic layer was dried over Na$_2$SO$_4$ and evaporated. Compound 4c was purified from this crude material by column chromatography (silicagel, n-hexane/EtOAc=3:1) (129.7 mg, 72.8%). $^1$H NMR (400 MHz, CDCl$_3$) δ 7.77-7.70 (m, 2H), 7.53 (d, J=8.0 Hz, 1H), 7.42 (ddd, J=8.0, 6.4, 1.6 Hz, 1H), 7.31-7.28 (m, 2H), 7.20-7.16 (m, 2H), 5.96 (br s, 1H), 3.92 (q, J=7.2, 6.8, 5.6 Hz, 2H), 3.01 (t, J=6.8 Hz, 2H). $^{13}$C NMR (100 MHz, CDCl$_3$) δ 160.8, 157.7, 150.9, 137.0, 133.6, 132.7, 130.2, 128.9, 127.9, 126.3, 120.5, 113.2, 42.4, 34.4. LC-MS (ESI, formic) m/z 318.0 [M+H]$^+$.

5c was obtained by taking a solution of 4c (50 mg, 0.157 mmol) in n-BuOH (2 mL) that was treated with DIEA (60.9 mg, 0.471 mmol) and L-prolinol (47.7 mg, 0.471 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 5c was purified from this crude material by column chromatography (silicagel, CH$_2$Cl$_2$:MeOH:triethylamine=10:1:0.1) (47.2 mg, 78.5%). purity (98.75%); $^1$H NMR (400 MHz, CDCl$_3$) δ 7.52-7.48 (m, 1H), 7.42 (d, J=8.0 Hz, 1H), 7.37 (d, J=7.6 Hz, 1H), 7.31-7.27 (m, 2H), 7.17 (d, J=7.6 Hz, 2H), 7.05-7.01 (m, 1H), 5.80 (br s, 1H), 4.40-4.35 (m, 1H), 3.98-3.91 (m, 1H), 3.86-3.78 (m, 3H), 3.72-3.62 (m, 2H), 3.00 (t, J=7.2, 6.8 Hz, 2H), 2.21-2.12 (m, 1H), 2.01-1.83 (m, 3H), 1.71-1.63 (m, 1H). $^{13}$C NMR (100 MHz, CDCl$_3$) δ 159.6, 158.5, 137.6, 133.0, 132.4, 130.2, 128.8, 121.2, 120.6, 110.1, 68.8, 61.1, 48.5, 42.4, 34.6, 29.9, 24.1. HRMS calcd for C$_{21}$H$_{24}$ClN$_4$O ([M+H]$^+$) m/z 383.1639, found m/z 383.1634; mp 101.6-104.6° C.

6c was obtained by taking a solution of 4c (50 mg, 0.157 mmol) in n-BuOH (2 mL) and was then treated with DIEA (60.9 mg, 0.471 mmol) and 2-piperidinemethanol (54.2 mg, 0.471 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 6c was purified from this crude material by column chromatography (silicagel, CH$_2$Cl$_2$:MeOH:triethylamine=10:1:0.1) (44.5 mg, 71.4%). purity (97.58%); $^1$H NMR (400 MHz, CDCl$_3$) δ 7.51-7.47 (m, 1H), 7.42 (d, J=8.0 Hz, 1H), 7.34 (d, J=8.0 Hz, 1H), 7.30-7.27 (m, 2H), 7.16 (d, J=8.4 Hz, 2H), 7.05-7.01 (m, 1H), 5.72 (br s, 1H), 5.07-5.02 (m, 1H), 4.79 (d, J=13.2 Hz, 1H), 4.11 (t, J=10.4, 10.0 Hz, 1H), 3.84-3.75 (m, 3H), 3.24-3.17 (m, 1H), 2.97 (t, J=7.2, 6.8 Hz, 2H), 1.75-1.71 (m, 3H), 1.69-1.54 (m, 3H). $^{13}$C NMR (100 MHz, CDCl$_3$) δ 160.3, 159.6, 151.1, 137.6, 132.8, 132.4, 130.2, 128.8, 125.3, 121.3, 120.5, 110.4, 64.3, 53.5, 42.4, 40.0, 34.7, 26.5, 25.3, 20.2. HRMS calcd for C$_{22}$H$_{26}$ClN$_4$O ([M+H]$^+$) m/z 397.1795, found m/z 397.1794; mp 153.2-155.3° C.

4d was then obtained by taking a solution of compound 3 (100 mg, 0.56 mmol) in n-BuOH (3 mL) and was then treated with DIEA (215.9 mg, 1.67 mmol) and 4-bromophenethylamine (112.0 mg, 0.56 mmol). The reaction mixture was stirred for 2 h at 40° C. and the solvent was evaporated. The residue was extracted with methylene chloride (30 mL, 3 times) and water. The organic layer was dried over Na$_2$SO$_4$ and evaporated. Compound 4d was purified by column chromatography (silicagel, n-hexane/EtOAc=3:1) (152.6 mg, 75.1%). $^1$H NMR (400 MHz, CDCl$_3$) δ 7.73-7.70 (m, 2H), 7.57 (d, J=8.0 Hz, 1H), 7.44-7.39 (m, 3H), 7.11 (d, J=8.4 Hz, 2H), 6.14 (br s, 1H), 3.91 (q, J=7.2, 6.8, 5.6 Hz, 2H), 2.99 (t, J=7.2, 6.8 Hz, 2H). $^{13}$C NMR (100 MHz, CDCl$_3$) δ 160.9, 157.7, 150.8, 137.5, 131.9, 130.6, 127.8, 126.3, 120.7, 120.6, 113.2, 42.4, 34.5. LC-MS (ESI, formic) m/z 362.0 [M+H]$^+$.

5d was then obtained by taking A solution of 4d (50 mg, 0.138 mmol) in n-BuOH (2 mL) and was then treated with DIEA (53.5 mg, 0.414 mmol) and L-prolinol (41.8 mg, 0.414 mmol). The reaction mixture was stirred overnight at 120° C. and the solvent was evaporated. The residue was dissolved in methylene chloride and extracted with water. The organic layer was dried over Na$_2$SO$_4$ and evaporated. Compound 5d was purified from this crude material by column chromatography (silicagel, CH$_2$Cl$_2$:MeOH:triethylamine=10:1:0.1) (47.3 mg, 80.2%). purity (98.43%); $^1$H NMR (400 MHz, CDCl$_3$) δ 7.56 (d, J=8.0 Hz, 1H), 7.48-7.40 (m, 4H), 7.10 (d, J=8.0 Hz, 2H), 7.04-7.00 (m, 1H), 4.40-4.36 (m, 1H), 3.91-3.85 (m, 1H), 3.82-3.77 (m, 3H), 3.71-3.60 (m, 2H), 2.97 (t, J=7.2 Hz, 2H), 2.19-2.10 (m, 1H), 2.03-1.84 (m, 2H), 1.75-1.67 (m, 1H). $^{13}$C NMR (100 MHz, CDCl$_3$) δ 159.5, 157.1, 138.1, 133.1, 131.7, 130.6, 121.7, 121.5, 120.4, 110.1, 68.0, 61.0, 48.5, 42.5, 34.6, 29.7, 23.9, 14.1. HRMS calcd for C$_{21}$H$_{24}$BrN$_4$O ([M+H]$^+$) m/z 427.1133, found m/z 427.1126.

6d was obtained by taking a solution of 4d (47.7 mg, 0.138 mmol) in n-BuOH (2 mL) and was then treated with DIEA (53.5 mg, 0.414 mmol) and 2-piperidinemethanol (41.8 mg, 0.414 mmol). The reaction mixture was stirred overnight at 120° C. and the solvent was evaporated. The residue was dissolved in methylene chloride and extracted with water. The organic layer was dried over Na$_2$SO$_4$ and evaporated. Compound 6d was purified from this crude material by column chromatography (silicagel, CH$_2$Cl$_2$:MeOH:triethylamine=10:1:0.1) (45.7 mg, 75.0%). purity (96.17%); $^1$H NMR (400 MHz, CDCl$_3$) δ 7.52-7.45 (m, 2H), 7.38 (d, J=8.0 Hz, 1H), 7.36-7.32 (m, 2H), 7.28-7.24 (m, 2H), 7.06-7.02 (m, 1H), 6.00 (br s, 1H), 5.05-5.01 (m, 1H), 4.82 (d, J=13.2 Hz, 1H), 4.11 (t, J=10.0 Hz, 1H), 3.86-3.78 (m, 3H), 3.23-3.16 (m, 1H), 3.01 (t, J=7.0 Hz, 2H), 1.78-

1.72 (m, 3H), 1.68-1.58 (m, 4H). $^{13}$C NMR (100 MHz, CDCl$_3$) δ 159.5, 139.0, 133.0, 128.8, 126.6, 121.7, 120.8, 110.3, 63.8, 53.7, 42.5, 40.0, 35.2, 29.7, 26.4, 25.3, 20.1. HRMS calcd for C$_{22}$H$_{26}$BrN$_4$O ([M+H]$^+$) m/z 441.1290, found m/z 441.1280; mp 141.3-145.3° C.

4e was then obtained by taking a solution of compound 3 (100 mg, 0.56 mmol) in n-BuOH (3 mL) and was then treated with DIEA (215.9 mg, 1.67 mmol) and 4-methylphenethylamine (75.7 mg, 0.56 mmol). The reaction mixture was stirred for 2 h at 40° C. and the solvent was evaporated. The residue was extracted with methylene chloride (20 mL, 3 times) and water. The organic layer was dried over Na$_2$SO$_4$ and evaporated. Compound 4e was purified from this crude material by column chromatography (silicagel, n-hexane/EtOAc=3:1) (122.5 mg, 73.5%). $^1$H-NMR (400 MHz, CDCl$_3$) δ 7.77-7.74 (m, 1H), 7.71 (ddd, J=8.4, 6.8, 1.6 Hz, 1H), 7.49 (d, J=8.4 Hz, 1H), 7.40 (ddd, J=8.4, 6.8, 1.6 Hz, 1H), 7.17-7.12 (m, 4H), 5.91 (br s, 1H), 3.92 (q, J=6.8 Hz, 2H), 2.99 (t, J=6.8 Hz, 2H), 2.35 (s, 3H). $^{13}$C NMR (100 MHz, CDCl$_3$) δ 160.8, 157.8, 150.8, 136.4, 135.3, 133.4, 129.6, 128.7, 127.9, 126.2, 120.5, 113.3, 42.5, 34.6, 21.1. LC-MS (ESI, formic) m/z 298.1 [M+H]$^+$.

5e was then obtained by taking a solution of 4e (50 mg, 0.168 mmol) in n-BuOH (2 mL) and was then treated with DIEA (65.1 mg, 0.504 mmol) and L-prolinol (51.0 mg, 0.504 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 5e was purified from this crude material by column chromatography (silicagel, CH$_2$Cl$_2$:MeOH:triethylamine=10:1:0.1) (41.2 mg, 67.7%). purity (98.80%); $^1$H NMR (400 MHz, CDCl$_3$) δ 7.48 (ddd, J=8.4, 6.8, 1.2 Hz, 1H), 7.41 (d, J=8.0 Hz, 1H), 7.36 (d, J=8.0 Hz, 1H), 7.16-7.12 (m, 4H), 7.01 (ddd, J=8.4, 6.8, 1.2 Hz, 1H), 5.86 (br s, 1H), 4.40-4.35 (m, 1H), 3.99-3.93 (m, 1H), 3.86-3.81 (m, 1H), 3.81-3.78 (m, 2H), 3.72-3.63 (m, 2H), 2.98 (t, J=7.0 Hz, 2H), 2.34 (s, 3H), 2.20-2.12 (m, 1H), 1.99-1.82 (m, 2H), 1.71-1.63 (m, 1H). $^{13}$C NMR (100 MHz, CDCl$_3$) δ 159.6, 158.5, 136.1, 136.0, 132.8, 129.4, 128.7, 124.6, 121.1, 120.7, 110.2, 68.8, 61.1, 48.5, 42.6, 34.8, 30.0, 29.7, 24.1, 21.1. HRMS (FAB) calcd for C$_{22}$H$_{27}$N$_4$O ([M+H]$^+$) m/z 363.2185, found m/z 363.2178; mp 144.2-146.6° C.

6e was then obtained by taking a solution of 4e (50 mg, 0.168 mmol) in n-BuOH (2 mL) and was then treated with DIEA (65.1 mg, 0.504 mmol) and 2-piperidinemethanol (58.0 mg, 0.504 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 6e was purified from this crude material by column chromatography (silicagel, CH$_2$Cl$_2$:MeOH:triethylamine=10:1:0.1) (44.7 mg, 70.1%). purity (97.12%); $^1$H NMR (400 MHz, CDCl$_3$) δ 7.49 (ddd, J=8.4, 6.8, 1.6 Hz, 1H), 7.42 (d, J=8.0 Hz, 1H), 7.32-7.30 (d, J=8.0 Hz, 1H), 7.17-7.12 (m, 4H), 7.04-7.00 (m, 1H), 5.62 (br s, 1H), 5.09-5.03 (m, 1H), 4.84-4.79 (m, 1H), 4.12 (t, J=10.4 Hz, 1H), 3.91-3.75 (m, 3H), 3.24-3.17 (m, 1H), 2.97 (t, J=7.2, 6.8 Hz, 2H), 2.35 (s, 3H), 1.78-1.72 (m, 3H), 1.67-1.56 (m, 4H). $^{13}$C NMR (100 MHz, CDCl$_3$) δ 159.6, 136.2, 135.9, 132.7, 129.5, 128.7, 121.1, 120.5, 53.5, 42.5, 40.0, 34.9, 29.7, 26.5, 25.3, 21.1, 20.3. HRMS (FAB) calcd for C$_{23}$H$_{29}$N$_4$O ([M+H]$^+$) m/z 377.2341, found m/z 377.2343; mp 143.1-146.8° C.

6f was then obtained by taking a solution of 4f (313 mg, 1 mmol)$^9$ in n-BuOH (15 mL) and was then treated with DIEA (388 mg, 3 mmol) and 2-piperidinemethanol (3.3 mg, 3 mmol). The reaction mixture was stirred overnight at 120° C. and the solvent was evaporated. The residue was extracted with methylene chloride (50 mL, 3 times) and water. The organic layer was dried over Na$_2$SO$_4$ and evaporated. Compound 6f was purified from this crude material by column chromatography (silicagel, CH$_2$Cl$_2$:MeOH:triethylamine=10:1:0.1) (262 mg, 69.5%). purity (96.93%); $^1$H NMR (400 MHz, CDCl$_3$) δ 7.50 (m, 1H), 7.44 (m, 1H), 7.32 (d, J=8.4 Hz, 1H), 7.16 (m, 1H), 6.88 (m, 2H), 5.95 (br s, 1H), 5.06 (m, 1H), 4.83 (m, 1H), 4.11 (m, 1H), 3.81 (s, 3H), 2.79 (m, 2H), 3.20 (m, 1H), 2.95 (m, 1H), 1.75 (m, 2H), 1.66 (m, 4H); $^{13}$C NMR (100 MHz, CDCl$_3$) δ 161.5, 159.6, 152.1, 138.7, 132.8, 128.8, 127.8, 127.6, 125.6, 121.1, 120.6, 110.4, 64.3, 53.4, 45.3, 40.0, 26.4, 25.3, 20.3. LC-MS ESI, formic) m/z 393.1 [M+H]$^+$. HRMS (FAB) calcd for C$_{23}$H$_{29}$N$_4$O$_2$ ([M+H]$^+$) m/z 392.2212, found m/z 392.2130.

9a was then obtained by taking a solution of 7a (270 mg, 1 mmol)$^{49}$ in n-BuOH (15 mL) and was then treated with DIEA (388 mg, 3 mmol) and 2-piperidinemethanol (3.3 g, 3 mmol). The reaction mixture was stirred overnight at 120° C. and the solvent was evaporated. The residue was extracted with methylene chloride (50 mL, 3 times) and water. The organic layer was dried over Na$_2$SO$_4$ and evaporated. Compound 9a was purified from this crude material by column chromatography (silicagel, CH$_2$Cl$_2$:MeOH:triethylamine=10:1:0.1) (212 mg, 60.9%). purity (100%); $^1$H NMR (400 MHz, CDCl$_3$) δ 7.52-7.32 (m, 8H), 7.04 (t, J=8.4 Hz, 1H), 5.80 (br s, 1H), 5.03 (t, J=4.8 Hz, 1H), 4.84-4.74 (m, 3H), 4.06 (t, J=10.8 Hz, 1H), 3.73 (t, J=6.8 Hz, 1H), 3.16 (m, 1H), 1.70-1.55 (m, 6H). $^{13}$C NMR (100 MHz, CDCl$_3$) δ 160.3, 159.5, 151.6, 137.2, 133.2, 132.8, 129.0, 128.8, 125.5, 121.2, 120.6, 110.4, 64.3, 53.4, 44.6, 40.0, 26.4, 25.2, 20.2. LC-MS (ESI, formic) m/z 349.2 [M+H]$^+$. HRMS (FAB) calcd for C$_{21}$H$_{25}$N$_4$O ([M+H]$^+$) m/z 349.2028, found m/z 349.1950.

9b was then obtained by taking a solution of 7b (304 mg, 1 mmol)$^{21}$ in n-BuOH (15 mL) and was then treated with DIEA (388 mg, 3 mmol) and 2-piperidinemethanol (345 mg, 3 mmol). The reaction mixture was stirred overnight at 120° C. and the solvent was evaporated. The residue was extracted with methylene chloride (50 mL, 3 times) and water. The organic layer was dried over Na$_2$SO$_4$ and evaporated. Compound 9b was purified from this crude material by column chromatography (silicagel, CH$_2$Cl$_2$:MeOH:triethylamine=10:1:0.1) (263 mg, 68.6%). purity (100%); $^1$H NMR (400 MHz, CDCl$_3$) δ 7.52-7.46 (m, 2H), 7.40 (d, J=8.0 Hz, 1H), 7.30-7.26 (m, 4H), 7.04 (t, J=7.6 Hz, 1H), 5.95 (br s, 1H), 4.98 (m, 1H), 4.80-4.69 (m, 3H), 4.06 (t, J=10.4 Hz, 1H), 3.73 (t, J=6.8 Hz, 1H), 3.14 (m, 1H), 1.70-1.51 (m, 6H). $^{13}$C NMR (100 MHz, CDCl$_3$) δ 161.3, 159.6, 158.4, 132.7, 131.0, 129.8, 125.4, 121.0, 120.5, 114.2, 110.6, 64.5, 55.3, 53.4, 42.6, 40.0, 34.4, 26.6, 25.3, 20.3. LC-MS (ESI, formic) m/z 383.1 [M+H]$^+$. HRMS (FAB) calcd for C$_{21}$H$_{24}$ClN$_4$O ([M+H]$^+$) m/z 383.1639, found m/z 383.1657.

4g was then obtained by following the general procedure. A solution of compound 3 (140 mg, 0.7 mmol) in n-BuOH (7 mL) was treated with DIEA (98.6 mg, 0.77 mmol) and 3-fluorophenethylamine (107 mg, 0.77 mmol). Compound 4g was purified from this crude material by column chromatography (silicagel, n-hexane/EtOAc=3:1) (128.2 mg, 60.8%). $^1$H-NMR (400 MHz, CDCl$_3$) δ 7.69-7.60 (m, 2H), 7.49 (d, J=8.0 Hz, 1H), 7.34 (t, J=8.0 Hz, 7.25-7.19 (m, 1H), 6.95 (d, J=7.6 Hz, 1H), 6.93-6.87 (m, 2H), 6.02 (s, 1H, —NH), 3.86 (dd, J=12.8, 6.8 Hz, 2H, —CH$_2$—), 2.96 (t, J=6.8 Hz, 2H, —CH$_2$—). $^{13}$C-NMR (100 MHz, CDCl$_3$) 5160.8, 157.7, 150.7, 141.1, 133.6, 130.2, 127.8, 126.3, 124.5, 120.6, 115.8, 113.8, 113.2, 42.3, 34.8. LC-MS (ESI, formic) m/z: 302.1 ([M+H]$^+$).

5f was then obtained by taking a solution of 4g (40 mg, 0.13 mmol) in n-BuOH (4 mL) and was then treated with DIEA (33.3 mg, 0.26 mmol) and L-prolinol (26.8 mg, 0.26 mmol). The reaction mixture was stirred 24 hrs at 120° C. and the solvent was evaporated. The residue was extracted with methylene chloride (10 mL, 3 times) and water. The organic layer was dried over Na$_2$SO$_4$ and evaporated. Compound 5f was purified from this crude material by prep-HPLC (UV 254 nm, 4.0 mL/min, H$_2$O/ACN (0.01% TFA) 5-60%, 0-30 min. (30.3 mg, 63.7%). purity (99.90%); $^1$H-NMR (400 MHz, CDCl$_3$) δ 12.38 (s, 1H, —OH), 9.37 (s, 1H, —NH), 8.00 (d, J=8.0 Hz, 1H), 7.42 (td, J=8.4, 0.8 Hz, 1H), 7.34-7.23 (m, 2H), 7.09 (td, J=8.0, 0.4 Hz, 1H), 7.03 (d, J=7.6 Hz, 1H), 6.95 (d, J=8.4 Hz, 2H), 4.29 (brs, 1H), 3.96-3.88 (m, 1H), 3.88-3.55 (m, 6H), 2.99 (t, J=8.0 Hz, 2H), 2.28-2.14 (m, 1H), 2.14-1.99 (m, 2H), 1.99-1.88 (m, 1H). $^{13}$C-NMR (100 MHz, CDCl$_3$) δ 164.8, 163.2, 162.8, 162.4, 159.7, 152.1, 141.8, 141.7, 139.2, 134.8, 130.8, 130.8, 125.2, 125.1, 124.8, 124.5, 117.7, 116.3, 116.1, 116.0, 114.3, 114.1, 110.2, 65.7, 61.9, 49.6, 43.5, 35.1, 29.8, 23.6. LC-MS (ESI, formic) m/z: 367.2 ([M+H]$^+$). HRMS (FAB) calcd for C$_{21}$H$_{24}$FN$_4$O ([M+H]$^+$) m/z: 367.1934, found m/z: 367.1936.

6g was then obtained by taking a solution of 4g (40 mg, 0.13 mmol) in n-BuOH (4 mL) and was then treated with DIEA (33.3 mg, 0.26 mmol) and 2-piperidinemethanol (27.0 g, 0.26 mmol). The reaction mixture was stirred 48 hrs at 120° C. and the solvent was evaporated. The residue was extracted with methylene chloride (10 mL, 3 times) and water. The organic layer was dried over Na$_2$SO$_4$ and evaporated. Compound 4g was purified from this crude material by prep-HPLC (UV 254 nm, 4.0 mL/min, H$_2$O/ACN (0.01% TFA) 5-60%, 0-30 min. (24.8 mg, 50.0%). purity (97.15%); $^1$H-NMR (400 MHz, CDCl$_3$+CD$_3$OD) δ 8.53 (s, 1H, —NH), 7.75 (d, J=8.0 Hz, 1H), 7.70 (d, J=8.4 Hz, 1H), 7.25-7.18 (m, 2H), 6.98 (d, J=12.0 Hz, 1H), 6.92-6.84 (m, 2H), 4.75 (s, 1H), 3.94 (dd, J=12.0, 10.0 Hz, 1H), 3.72-3.70 (m, 3H), 3.34-3.25 (m, 2H), 3.13 (m, 1H), 2.95 (t, J=7.2 Hz, 2H, benzylic-CH$_2$), 1.90-1.80 (m, 2H), 1.79-1.43 (m, 4H). $^{13}$C-NMR (100 MHz, CDCl$_3$+CD$_3$OD) δ 164.1, 161.7, 159.4, 152.7, 141.1, 141.0, 139.5, 134.8, 130.2, 130.1, 124.6, 124.4, 124.3, 122.5, 117.9, 115.6, 115.3, 113.6, 113.4, 109.6, 60.1, 54.6, 42.9, 40.3, 34.4, 25.3, 25.1, 19.0. LC-MS (ESI, formic) m/z: 381.2 ([M+H]$^+$). HRMS (FAB) calcd for C$_{22}$H$_{26}$FN$_4$O ([M+H]$^+$) m/z: 381.2091, found m/z: 381.2088.

4h was obtained by following the general procedure. A solution of compound 3 (140 mg, 0.7 mmol) in n-BuOH (6 mL) was treated with DIEA (98.6 mg, 0.77 mmol) and 3-chlorophenethylamine (120 mg, 0.77 mmol). Compound 4h was purified from this crude material by column chromatography (silicagel, n-hexane/EtOAc=3:1) (142.2 mg, 64.1%). $^1$H-NMR (400 MHz, CDCl$_3$) δ 7.81-7.72 (m, 2H), 7.62 (d, J=8.0 Hz, 1H), 7.47 (t, J=8.0 Hz, 1H), 7.31-7.21 (m, 2H), 7.15 (dd, J=6.0, 1.6 Hz, 1H), 6.39 (s, 1H, —NH), 3.94 (dd, J=12.8, 7.2 Hz, 2H, —CH$_2$—), 3.04 (t, J=7.2 Hz, 2H, —CH$_2$—). $^{13}$C-NMR (100 MHz, CDCl$_3$) δ 160.7, 157.2, 149.8, 140.5, 134.6, 133.8, 130.1, 129.0, 127.0, 126.5, 120.8, 113.0, 42.5, 34.7. LC-MS (ESI, formic) m/z: 318.1 ([M+H]$^+$).

5g was then obtained by following the general procedure. A solution of 4h (40 mg, 0.13 mmol) in n-BuOH (4 mL) was treated with DIEA (33.3 mg, 0.26 mmol) and L-prolinol (25.5 mg, 0.26 mmol). Compound 5g was purified from this crude material by prep-HPLC (UV 254 nm, 4.0 mL/min, H$_2$O/ACN (0.01% TFA) 5-60%, 0-30 min), (30.4 mg, 61.2%). purity (99.90%); $^1$H-NMR (400 MHz, CDCl$_3$) δ 12.63 (s, 1H), 9.47 (s, 1H), 8.01 (d, J=8.0 Hz, 1H), 7.42 (t, J=8.0, 0.8 Hz, 1H), 7.29-7.17 (m, 4H), 7.17-7.07 (m, 2H), 4.27 (s, 1H), 4.06 (brs, 1H), 3.89 (s, 1H), 3.82-3.57 (m, 4H), 2.97 (t, J=7.6 Hz, 2H, benzyl-CH$_2$—), 2.28-2.10 (m, 1H), 2.10-1.97 (m, 2H), 1.97-1.88 (m, 1H). $^{13}$C-NMR (100 MHz, CDCl$_3$) δ 163.5, 163.1, 162.8, 162.4, 159.8, 152.1, 141.3, 139.2, 135.0, 134.8, 129.5, 127.7, 127.4, 124.8, 124.5, 118.9, 117.7, 116.0, 110.2, 65.7, 62.0, 49.6, 43.6, 35.1, 29.8, 23.6. LC-MS (ESI, formic) m/z: 383.2 ([M+H]$^+$). HRMS (FAB) calculated for C$_{21}$H$_{24}$ClN$_4$O ([M+H]$^+$) m/z: 383.1639, found m/z: 383.1635.

6h was then obtained by following the general procedure. A solution of 4h (40 mg, 0.12 mmol) in n-BuOH (4 mL) was treated with DIEA (30.7 mg, 0.24 mmol) and 2-piperidinemethanol (26.0 mg, 0.24 mmol). Compound 6h was purified from this crude material by prep-HPLC (UV 254 nm, 4.0 mL/min, H$_2$O/ACN (0.01% TFA) 5-60%, 0-30 min). (29.8 mg, 62.5%). purity (99.50%); $^1$H-NMR (400 MHz, CDCl$_3$+CD$_3$OD) δ 8.65 (brs, 1H, —NH), 7.75 (d, J=8.4 Hz, 1H), 7.61 (d, J=8.4 Hz, 1H), 7.50 (t, J=8.4 Hz, 1H), 7.23-7.15 (m, 4H), 7.09-7.00 (m, 1H), 4.72 (s, 1H), 3.96 (dd, J=12.0, 10.0 Hz, 1H), 3.78-3.63 (m, 3H), 3.35 (s, 2H), 3.14 (s, 1H), 2.91 (t, J=7.6 Hz, 2H), 1.80-1.76 (m, 2H), 1.70-1.45 (m, 4H). $^{13}$C-NMR (100 MHz, CDCl$_3$+CD$_3$OD) δ 159.4, 152.6, 140.6, 139.4, 134.7, 134.3, 129.9, 128.7, 126.9, 126.8, 124.6, 122.7, 117.7, 109.5, 60.1, 54.7, 42.9, 40.2, 34.3, 25.3, 25.0, 19.0. LC-MS (ESI, formic) m/z: 397.2 ([M+H]$^+$). HRMS (FAB) calculated for C$_{22}$H$_{26}$ClN$_4$O ([M+H]$^+$) m/z: 397.1795, found m/z: 397.1802.

4i was then obtained by following the general procedure. A solution of compound 3 (140 mg, 0.7 mmol) in n-BuOH (6 mL) was treated with DIEA (98.6 mg, 0.77 mmol) and 3-bromophenethylamine (154 mg, 0.77 mmol). Compound 4i was purified from this crude material by column chromatography (silicagel, n-hexane/EtOAc=3:1) (128.2 mg, 50.7%). $^1$H-NMR (400 MHz, CDCl$_3$) δ 7.71-762 (m, 2H), 7.49 (d, J=8.4 Hz, 1H), 7.38-7.30 (m, 2H), 7.14-7.08 (m, 1H), 5.99 (s, 1H, —NH), 3.86 (dd, J=12.4, 6.8 Hz, 2H, —CH$_2$—), 2.94 (t, J=7.2 Hz, 2H, —CH$_2$—). $^{13}$C-NMR (100 MHz, CDCl$_3$) δ 159.8, 156.7, 149.8, 147.2, 140.9, 139.9, 132.6, 130.9, 129.3, 128.9, 126.5, 125.3, 121.8, 119.6, 112.2, 41.3, 33.7. LC-MS (ESI) m/z: 362.0 ([M+H]$^+$);

5h was then obtained by following the general procedure. A solution of 4i (40 mg, 0.11 mmol) in n-BuOH (4 mL) was treated with DIEA (28.6 mg, 0.22 mmol) and L-prolinol (22.3 mg, 0.22 mmol). Compound 5h was purified from this crude material by prep-HPLC (UV 254 nm, 4.0 mL/min, H$_2$O/ACN (0.01% TFA) 5-60%, 0-30 min), (19.8 mg, 40.8%). purity (99.90%); $^1$H-NMR (400 MHz, CDCl$_3$) δ 12.35 (brs, 1H), 9.28 (brs, 1H, —NH), 7.99 (d, J=8.0, 1H), 7.48-7.35 (m, 3H), 7.26 (brs, 1H), 7.21-7.15 (m, 2H), 4.29 (brs, 1H), 3.97-3.74 (m, 3H), 3.75-3.58 (m, 1H), 3.42 (brs, 3H), 2.97 (t, J=7.6 Hz, 2H, benzyl-CH$_2$—), 2.29-2.15 (m, 1H), 2.12-1.88 (m, 3H). $^{13}$C-NMR (100 MHz, CDCl$_3$+CD$_3$OD) δ 159.5, 141.0, 134.6, 131.7, 130.2, 129.6, 127.5, 124.5, 123.4, 122.5, 121.5, 117.3, 109.5, 64.2, 60.9, 48.9, 42.8, 34.4. 28.5, 22.8. LC-MS (ESI, formic) m/z: 427.1 ([M+H]$^+$). HRMS (FAB) calcd for C$_{21}$H$_{24}$BrN$_4$O ([M+H]$^+$) m/z 427.1133, found m/z 427.1132.

6i was then obtained by following the general procedure. A solution of 4i (40 mg, 0.11 mmol) in n-BuOH (4 mL) was treated with DIEA (28.2 mg, 0.22 mmol) and 2-piperidinemethanol (24.0 mg, 0.22 mmol). Compound 6i was purified from this crude material by prep-HPLC (UV 254 nm, 4.0 mL/min, H$_2$O/ACN (0.01% TFA) 5-60%, 0-30 min), (19.8 mg, 40.8%). purity (99.39%); $^1$H-NMR (400 MHz, CDCl$_3$) δ 12.08 (brs, 1H), 8.46 (s, 1H), 7.71 (d, J=7.6 Hz, 1H), 7.49 (d, J=8.0 Hz, 1H), 7.44-7.32 (m, 3H), 7.24-7.08 (m, 3H), 4.74 (brs, 1H), 4.09 (t, J=10.8 Hz, 1H), 3.88 (s, 1H), 3.71 (s, 1H), 3.61-3.49 (m, 1H), 3.31 (s, 2H), 3.14 (s, 1H), 2.92 (t, J=7.6 Hz, 2H, benzyl-CH$_2$—), 1.95-1.79 (m, 2H), 1.78-1.48 (m, 4H). $^{13}$C-NMR (100 MHz, CDCl$_3$) δ 159.7, 153.2, 141.4, 139.8, 135.2, 132.3, 131.0, 130.5, 128.0, 125.3, 123.6, 123.3, 118.3, 109.9, 61.4, 55.7, 43.6, 40.8, 35.0, 26.3, 25.7, 19.8. LC-MS (ESI, formic) m/z: 441.1 ([M+H]$^+$). HRMS (FAB) calcd for C$_{22}$H$_{26}$BrN$_4$O ([M+H]$^+$) m/z: 441.1290; found m/z: 441.1290.

4j was then obtained by following the general procedure. A solution of compound 3 (140 mg, 0.7 mmol) in n-BuOH (6 mL) was treated with DIEA (98.6 mg, 0.77 mmol) and 3-methoxyphenethylamine (118 mg, 0.77 mmol). Compound 4j was purified from this crude material by column chromatography (silicagel, n-hexane/EtOAc=3:1) (128.5 mg, 57.8%). $^1$H-NMR (400 MHz, CDCl$_3$) δ 7.66-7.58 (m, 2H), 7.47 (d, J=8.0 Hz, 1H), 7.31 (t, J=8.4 Hz, 1H), 7.16 (t, J=8.8 Hz, 1H), 6.73-6.70 (m, 2H), 6.09 (s, 1H, —NH), 3.84 (dd, J=12.4, 6.8 Hz, 2H, —CH$_2$—), 3.70 (s, 3H, —OCH$_3$), 2.92 (t, J=6.8 Hz, 2H). $^{13}$C-NMR (100 MHz, CDCl$_3$) δ 160.9, 160.0, 157.8, 150.8 140.1, 133.5, 129.8, 127.7, 126.2, 121.1, 120.7, 114.5, 113.3, 112.2, 55.2, 42.4, 35.1. LC-MS (ESI) m/z: 314.1 ([M+H]$^+$).

5i was then obtained by following the general procedure. A solution of 4j (40 mg, 0.13 mmol) in n-BuOH (4 mL) was treated with DIEA (33.3 mg, 0.26 mmol) and L-prolinol (25.9 mg, 0.26 mmol). Compound 5i was purified from this crude material by prep-HPLC (UV 254 nm, 4.0 mL/min, H$_2$O/ACN (0.01% TFA) 5-60%, 0-30 min), (29.3 mg, 59.6%). purity (99.80%); $^1$H-NMR (400 MHz, CD$_3$OD) δ 8.06 (dd, J=8.0, 1.2 Hz, 1H), 7.80 (dd, J=8.4, 1.2 Hz, 1H), 7.44 (td, J=8.0, 0.8 Hz, 1H), 7.19 (t, J=7.6 Hz, 1H), 6.88-6.81 (m, 2H), 6.80-6.73 (m, 1H), 3.98-3.90 (m, 2H), 3.90-3.85 (m, 1H), 3.73 (s, 3H), 3.02 (t, J=7.2 Hz, 2H), 2.40-1.90 (m, 4H). $^{13}$C-NMR (100 MHz, CDCl$_3$+CD$_3$OD) δ 159.7, 159.2, 140.2, 134.5, 129.6, 124.5, 123.4, 121.0, 117.2, 114.6, 111.8, 109.6, 64.27, 61.0, 55.1, 50.0, 43.2, 34.7, 28.9, 22.6. LC-MS (ESI, formic) m/z: 379.2 ([M+H]$^+$). HRMS (FAB) calculated for C$_{22}$H$_{27}$N$_4$O$_2$ ([M+H]$^+$) m/z: 379.2134, found m/z: 379.2132.

6j was then obtained by following the general procedure. A solution of 4j (40 mg, 0.13 mmol) in n-BuOH (4 mL) was treated with DIEA (28.2 mg, 0.26 mmol) and 2-piperidinemethanol (26.0 mg, 0.26 mmol). Compound 6j was purified from this crude material by prep-HPLC (UV 254 nm, 4.0 mL/min, H$_2$O/ACN (0.01% TFA) 5-60%, 0-30 min), (32.1 mg, 62.7%). purity (96.76%); $^1$H-NMR (400 MHz, CDCl$_3$+CD$_3$OD) δ 7.68 (d, J=8.0 Hz, 2H), 7.51 (m, 1H), 7.24-7.15 (m, 2H), 6.70-6.80 (m, 3H), 4.78 (s, 1H), 4.05-3.90 (m, 1H), 3.75 (s, 3H), 3.20-3.10 (m, 1H), 2.95-2.85 (m, 4H) 1.90-1.80 (m, 2H), 1.80-1.45 (m, 4H). $^{13}$C-NMR (100 MHz, CDCl$_3$+CD$_3$OD) δ 159.8, 159.2, 140.0, 139.5, 134.7, 129.7, 124.6, 122.4, 121.0, 118.0, 114.6, 111.8, 109.4, 60.1, 55.1, 54.7, 43.1, 34.7, 25.4, 25.1, 19.1. LC-MS (ESI, formic) m/z: 393.2 ([M+H]$^+$). HRMS (FAB) calculated for C$_{22}$H$_{29}$N$_4$O$_2$ ([M+H]$^+$) m/z: 393.2291, found m/z: 393.2285.

4k was then obtained by following the general procedure. A solution of compound 3 (140 mg, 0.7 mmol) in n-BuOH (6 mL) was treated with DIEA (98.6 mg, 0.77 mmol) and 2-fluorophenethylamine (107 mg, 0.77 mmol). Compound 4k was purified from this crude material by column chromatography (silicagel, n-hexane/EtOAc=3:1) (137.2 mg, 65.1%). $^1$H-NMR (400 MHz, CDCl$_3$) δ 7.68-7.58 (m, 2H), 7.52 (d, J=8.0 Hz, 1H), 7.34 (t, J=8.4 Hz, 1H), 7.20-7.11 (m, 2H), 7.06-6.94 (m, 2H), 6.13 (s, 1H, —NH), 3.84 (dd, J=12.4, 6.4 Hz, 2H, —CH$_2$—), 3.01 (t, J=6.4 Hz, 2H, —CH$_2$—). $^{13}$C-NMR (100 MHz, CDCl$_3$) δ 161.0, 157.7, 150.8, 133.5, 131.3, 128.7, 128.7, 127.7, 126.2, 125.6, 124.5, 120.7, 115.6, 115.4, 113.3, 41.8, 28.5. LC-MS (ESI) m/z: 302.1 ([M+H]$^+$).

5j was then obtained by following the general procedure. A solution of 4k (50 mg, 0.16 mmol) in n-BuOH (4 mL) was treated with DIEA (42.2 mg, 0.33 mmol) and L-prolinol (34 mg, 0.33 mmol). Compound 5j was purified from this crude material by prep-HPLC (UV 254 nm, 4.0 mL/min, H$_2$O/ACN (0.01% TFA) 5-60%, 0-30 min), (47.1 mg, 77.5%). purity (96.39%); $^1$H-NMR (400 MHz, CDCl$_3$) δ 8.05 (dd, J=8.4, 0.8, 1H), 7.81 (t, J=8.4 Hz, 1H), 7.45 (t, J=8.4 Hz, 1H), 7.38-7.22 (m, 2H), 7.13-7.01 (m, 2H), 4.00-3.85 (m, 3H), 3.85-3.67 (m, 2H), 3.14 (t, J=7.2 Hz, 2H), 2.38-1.89 (m, 6H). $^{13}$C-NMR (100 MHz, CDCl$_3$) δ 162.3, 160.3, 159.5, 151.1, 139.0, 134.5, 131.3, 131.2, 128.5, 128.4, 125.8, 124.5, 124.3, 123.5, 117.4, 115.4, 115.2, 109.4, 64.2, 60.7, 41.8, 28.9, 28.5, 22.6. LC-MS (ESI, formic) m/z: 367.2 ([M+H]$^+$). HRMS (FAB) calculated for C$_{21}$H$_{24}$FN$_4$O ([M+H]$^+$) m/z: 367.1934, found m/z: 367.1937.

6k was then obtained by following the general procedure. A solution of 4k (50 mg, 0.16 mmol) in n-BuOH (4 mL) was treated with DIEA (42.2 mg, 0.33 mmol) and 2-piperidinemethanol (38.0 mg, 0.33 mmol). Compound 6k was purified from this crude material by prep-HPLC (UV 254 nm, 4.0 mL/min, H$_2$O/ACN (0.01% TFA) 5-60%, 0-30 min), (31.1 mg, 49.2%). purity (97.27%); $^1$H-NMR (400 MHz, CDCl$_3$+CD$_3$OD) δ 8.46 (t, J=5.2 Hz, 1H, —NH), 7.71 (d, J=8.4 Hz, 1H), 7.63 (d, J=8.4 Hz, 1H), 7.52 (t, J=8.4 Hz, 1H), 7.25-7.15 (m, 3H), 7.08-6.97 (m, 2H), 4.76 (s, 2H), 3.97 (dd, J=12.0, 10.0 Hz, 1H), 3.83-3.65 (m, 3H), 3.18-2.92 (m, 3H), 1.87-1.78 (m, 2H), 1.78-1.40 (m, 4H). $^{13}$C-NMR (100 MHz, CDCl$_3$+CD$_3$OD) δ 162.5, 160.1, 159.4, 152.6, 139.5, 134.7, 131.2, 131.1, 128.6, 128.5, 125.3, 125.2, 124.6, 124.4, 124.3, 122.4, 117.9, 115.5, 115.2, 109.4, 60.1, 54.6, 41.8, 28.5, 25.4, 25.1, 19.0. LC-MS (ESI, formic) m/z: 381.2 ([M+H]$^+$). HRMS (FAB) calculated for C$_{22}$H$_{26}$FN$_4$O ([M+H]$^+$) m/z: 381.2091, found m/z: 381.2090.

4l was then obtained by following the general procedure. A solution of compound 3 (160 mg, 0.81 mmol) in n-BuOH (6 mL) was treated with DIEA (114 mg, 0.89 mmol) and 2-chlorophenethylamine (126 mg, 0.81 mmol). Compound 4l was purified from this crude material by column chromatography (silicagel, n-hexane/EtOAc=3:1) (142.5 mg, 55.5%). $^1$H-NMR (400 MHz, CDCl$_3$) δ 7.83-7.70 (m, 2H), 7.59 (d, J=8.0 Hz, 1H), 7.50-7.38 (m, 2H), 7.34-7.27 (m, 2H), 7.27-7.20 (m, 2H). 6.07 (s, 1H, —NH), 4.00 (dd, J=12.4, 6.8 Hz, 2H), 3.23 (t, J=6.8 Hz, 2H). $^{13}$C-NMR (100 MHz, CDCl$_3$) δ 161.0, 158.0, 151.2, 148.0, 136.4, 134.1, 133.5, 131.2, 129.8, 128.4, 127.9, 127.3, 126.3, 120.6, 41.6, 32.6. LC-MS (ESI) m/z: 318.1 ([M+H]$^+$).

5k was then obtained by following the general procedure. A solution of 4l (50 mg, 0.16 mmol) in n-BuOH (4 mL) was treated with DIEA (41 mg, 0.32 mmol) and L-prolinol (33 mg, 0.32 mmol). Compound 5k was purified from this crude material by prep-HPLC (UV 254 nm, 4.0 mL/min, H$_2$O/ACN (0.01% TFA) 5-60%, 0-30 min), (38.7 mg, 63.3%). purity (99.90%); $^1$H-NMR (400 MHz, CDCl$_3$+CD$_3$OD) δ 7.83 (d, J=8.0 Hz, 1H), 7.42 (t, J=7.2 Hz, 1H), 7.33 (m, 1H), 7.30-7.26 (m, 1H), 7.20-7.17 (m, 1H), 7.13-7.07 (m, 3H), 4.24 (brs, 1H), 3.90-3.65 (m, 4H), 3.65-3.55 (m, 2H), 3.05 (t, J=7.2 Hz, 2H), 2.13-2.0 (m, 1H), 2.0-1.80 (m, 3H). $^{13}$C-NMR (100 MHz, CDCl$_3$+CD$_3$OD) δ 159.3, 151.5, 138.5, 136.2, 134.5, 134.0, 131.1, 129.5, 128.2, 127.1, 124.4, 123.3, 117.3, 109.4, 64.3, 60.9, 41.3, 32.7, 28.9, 22.7. LC-MS (ESI, formic) m/z: 383.2 ([M+H]$^+$). HRMS (FAB) calculated for $C_{21}H_{24}ClN_4O$ ([M+H]$^+$) m/z: 383.1639, found m/z: 383.1642.

6l was then obtained by following the general procedure. A solution of 4l (50 mg, 0.16 mmol) in n-BuOH (4 mL) was treated with DIEA (41 mg, 0.32 mmol) and 2-piperidinemethanol (37.0 mg, 0.32 mmol). Compound 6l was purified from this crude material by prep-HPLC (UV 254 nm, 4.0 mL/min, H$_2$O/ACN (0.01% TFA) 5-60%, 0-30 min), (28.7 mg, 45.3%). purity (96.99%); $^1$H-NMR (400 MHz, CDCl$_3$+CD$_3$OD) δ 8.48 (s, 1H, —NH), 7.73 (d, J=8.0 Hz, 1H), 7.70 (d, J=8.4 Hz, 1H), 7.52 (t, J=7.2 Hz, 1H), 7.36-7.30 (m, 1H), 7.25-7.12 (m, 4H), 4.76 (s, 1H), 3.95 (t, J=11.6 Hz, 1H), 3.90-3.80 (m, 1H), 3.80-3.70 (m, 2H), 3.25-3.10 (m, 2H), 3.10 (t, J=7.6 Hz, 2H), 1.90-1.80 (m, 2H), 1.78-1.45 (m, 4H). $^{13}$C-NMR (100 MHz, CDCl$_3$+CD$_3$OD) δ 159.4, 152.6, 139.5, 136.1, 134.7, 134.0, 131.0, 129.6, 128.3, 127.1, 124.6, 122.5, 117.9, 109.5, 60.1, 54.6, 41.3, 40.2, 32.8, 25.4, 25.1, 19.0. LC-MS (ESI, formic) m/z: 397.2 ([M+H]$^+$). HRMS (FAB) calcd for $C_{22}H_{26}ClN_4O$ ([M+H]$^+$) m/z: 397.1795, found m/z: 397.1799.

4m was then obtained by following the general procedure. A solution of compound 3 (160 mg, 0.81 mmol) in n-BuOH (6 mL) was treated with DIEA (114 mg, 0.89 mmol) and 2-chlorophenethylamine (162 mg, 0.81 mmol). Compound 4m was purified from this crude material by column chromatography (silicagel, n-hexane/EtOAc=3:1) (118.6 mg, 40.1%). $^1$H-NMR (400 MHz, DMSO-d$_6$) δ 8.88 (t, J=5.2 Hz, 1H, N—H), 8.21 (d, J=7.6 Hz, 1H), 7.79 (t, J=8.4 Hz, 1H), 7.58 (t, J=15.6 Hz, 2H), 7.52 (t, J=8.4 Hz, 1H), 7.40-7.26 (m, 2H), 7.16 (td, J=8.6, 2.0 Hz, 1H), 3.70-3.60 (m, 2H, —CH$_2$—), 3.11 (t, J=7.6 Hz, 2H, —CH$_2$—). $^{13}$C-NMR (100 MHz, DMSO-d$_6$) δ161.6, 157.4, 150.7, 138.8, 134.1, 133.0, 131.6, 129.0, 128.3, 127.1, 126.6, 124.5, 123.5, 114.0, 41.2, 34.8; LRMS (ESI) m/z: 363.2 ([M+H]$^+$).

5l was then obtained by following the general procedure. A solution of 4m (40 mg, 0.11 mmol) in n-BuOH (4 mL) was treated with DIEA (28 mg, 0.22 mmol) and L-prolinol (23 mg, 0.22 mmol). Compound 5l was purified from this crude material by prep-HPLC (UV 254 nm, 4.0 mL/min, H$_2$O/ACN (0.01% TFA) 5-60%, 0-30 min), (28.4 mg, 60.6%). purity (98.73%); $^1$H-NMR (400 MHz, CDCl$_3$+CD$_3$OD) δ 7.86 (d, J=7.6 Hz, 1H), 7.45 (d, J=8.0 Hz, 1H), 7.40 (t, J=8.0 Hz, 1H), 7.29 (brs, 1H), 7.21-7.11 (m, 2H), 7.08 (t, J=7.8 Hz, 1H), 7.00 (dd, J=7.6, 1.6 Hz, 1H), 4.21 (brs, 1H), 3.82-3.65 (m, 4H), 3.65-3.52 (m, 2H), 3.06 (t, J=7.2 Hz, 2H), 2.20-2.00 (m, 1H), 2.00-1.75 (m, 3H). $^{13}$C-NMR (100 MHz, CDCl$_3$+CD$_3$OD) δ 159.3, 151.3, 138.7, 138.0, 134.5, 132.8, 131.1, 128.4, 127.7, 124.4, 123.4, 118.1, 117.2, 109.5, 64.4, 61.0, 50.3, 41.5, 41.4, 35.1, 28.9, 22.7. LC-MS (ESI, formic) m/z: 427.1 ([M+H]$^+$). HRMS (FAB) calcd for $C_{21}H_{23}BrN_4O$ ([M+H]$^+$) m/z: 427.1133, found m/z: 427.1134.

6m was then obtained by following the general procedure. A solution of 4m (40 mg, 0.11 mmol) in n-BuOH (4 mL) was treated with DIEA (28.2 mg, 0.32 mmol) and 2-piperidinemethanol (25.3 mg, 0.22 mmol). Compound 6l was purified from this crude material by prep-HPLC (UV 254 nm, 4.0 mL/min, H$_2$O/ACN (0.01% TFA) 5-60%, 0-30 min), (19.8 mg, 40.9%). purity (98.30%); $^1$H-NMR (400 MHz, CDCl$_3$+CD$_3$OD) δ 8.25 (brs, 1H, —NH), 7.73-7.64 (m, 2H), 7.55 (d, J=7.6 Hz, 1H), 7.47 (t, J=7.6 Hz, 1H), 7.27-7.19 (m, 2H), 7.19-7.08 (m, 2H), 4.86 (brs, 1H, —OH), 4.01 (t, J=11.6 Hz, 1H), 3.78-3.67 (m, 1H), 3.13 (t, J=7.2 Hz, 3H), 1.90-1.78 (m, 2H), 1.78-1.40 (m, 4H). $^{13}$C-NMR (100 MHz, CDCl$_3$+CD$_3$OD) δ 159.2, 137.9, 134.6, 133.0, 131.1, 128.6, 127.8, 124.6, 124.4, 122.4, 118.0, 109.2, 60.3, 41.3, 35.3, 25.5, 25.3, 19.1. LC-MS (ESI, formic) m/z: 441.1 ([M+H]$^+$). HRMS (FAB) calcd for ([M+H]$^+$) $C_{22}H_{25}BrN_4O$ m/z: 441.1290, found m/z: 441.1287.

4n was then obtained by following the general procedure. A solution of compound 3 (160 mg, 0.81 mmol) in n-BuOH (6 mL) was treated with DIEA (114 mg, 0.89 mmol) and 2-methoxyphenethylamine (122 mg, 0.81 mmol). Compound 4n was purified from this crude material by column chromatography (silicagel, n-hexane/EtOAc=3:1) (134.3 mg, 53.0%). $^1$H-NMR (400 MHz, CDCl$_3$) δ 7.68-7.58 (m, 2H), 7.45 (d, J=8.0 Hz, 1H), 7.33 (t, J=8.0 Hz, 1H), 7.20-7.15 (m, 1H), 7.12 (dd, J=7.2, 1.2 Hz, 1H), 6.91-6.81 (m, 2H), 6.50 (s, 1H, —NH), 3.85 (s, 3H, —OCH$_3$), 3.78 (m, 2H, —CH$_2$—), 2.99 (t, J=6.4 Hz, 2H, —CH$_2$—). $^{13}$C-NMR (100 MHz, CDCl$_3$) δ 160.9, 157.9, 157.3, 150.7, 133.2, 130.9, 128.3, 127.8, 127.5, 125.9, 121.4, 120.6, 113.4, 110.9, 55.7, 43.0, 29.4. LC-MS (ESI) m/z: 314.1 ([M+H]$^+$).

5m was then obtained by following the general procedure. A solution of 4n (40 mg, 0.11 mmol) in n-BuOH (4 mL) was treated with DIEA (28.2 mg, 0.22 mmol) and L-prolinol (22 mg, 0.22 mmol). Compound 5l was purified from this crude material by prep-HPLC (UV 254 nm, 4.0 mL/min, H$_2$O/ACN (0.01% TFA) 5-60%, 0-30 min), (28.1 mg, 67.5%). purity (99.90%); $^1$H-NMR (400 MHz, CD$_3$OD) δ 8.04 (d, J=8.0, 0.8 Hz, 1H), 7.79 (td, J=10.0, 1.6 Hz, 1H), 7.43 (td, J=8.0, 0.8 Hz, 1H), 7.25-7.13 (m, 3H), 6.92 (d, J=7.6 Hz, 1H), 6.84 (td, J=7.6, 1.2 Hz, 1H), 4.48 (s, 1H), 4.00-3.85 (m, 3H), 3.75 (s, 3H), 3.75-3.60 (m, 2H), 3.33 (d, J=6.8, 2H, —CH$_2$—NH), 3.08 (t, J=6.8 Hz, 2H, benzylic), 2.4-1.90 (m, 4H). $^{13}$C-NMR (100 MHz, CDCl$_3$+CD$_3$OD) δ 159.3, 157.4, 134.7, 130.6, 128.1, 127.0, 124.5, 122.8, 120.9, 117.6, 110.6, 109.5, 63.9, 60.8, 55.4, 42.6, 42.4, 29.4, 28.7, 22.5. LC-MS (ESI, formic) m/z: 379.2 ([M+H]$^+$). HRMS (FAB) calcd for $C_{22}H_{27}N_4O_2$ ([M+H]$^+$) m/z: 379.2134, found m/z: 379.2134.

6n was then obtained by following the general procedure. A solution of 4m (40 mg, 0.11 mmol) in n-BuOH (4 mL) was treated with DIEA (28.2 mg, 0.32 mmol) and 2-piperidinemethanol (25.3 g, 0.22 mmol). Compound 6l was purified from this crude material by prep-HPLC (UV 254 nm, 4.0 mL/min, H$_2$O/ACN (0.01% TFA) 5-60%, 0-30 min), (17.7 mg, 41.0%). purity (95.10%); $^1$H-NMR (400 MHz, CDCl$_3$+CD$_3$OD) δ 8.02 (s, 1H, —NH), 7.85 (d, J=8.4 Hz, 1H), 7.65-7.52 (m, 2H), 7.28-7.7.18 (m, 2H), 7.13 (d, J=7.2 Hz, 1H), 6.97-6.84 (m, 2H), 4.82 (s, 1H), 3.94 (dd, J=12.0, 10.0 Hz, 1H), 3.82 (s, 3H), 3.82-3.70 (m, 3H), 3.18-3.05 (m, 3H), 3.01 (t, J=6.8 Hz, 2H), 1.90-1.78 (m, 2H), 1.76-1.45 (m, 4H). $^{13}$C-NMR (100 MHz, CDCl$_3$+CD$_3$OD) δ 159.2, 157.4, 152.6, 139.7, 134.8, 130.6, 128.3, 127.0, 124.5, 121.9, 121.1, 118.3, 110.8, 109.5, 60.0, 55.5, 54.6, 42.6, 40.2, 29.4, 25.3, 25.1, 19.0. LC-MS (ESI, formic) m/z: 393.2 ([M+H]$^+$). HRMS (FAB) calcd for $C_{23}H_{29}N_4O_2$ ([M+H]$^+$) m/z: 393.2291, found m/z: 393.2292.

7d was then obtained by following the general general procedure. A solution of compound 3 (160 mg, 0.81 mmol) in n-BuOH (6 mL) was treated with DIEA (114 mg, 0.89 mmol) and 3,4-dimethoxybenzylamine (142.2 mg, 0.85 mmol). Compound 7d was purified from this crude material by column chromatography (silicagel, n-hexane/EtOAc=3:1) (213.2 mg, 80.0%). $^1$H-NMR (400 MHz, CDCl$_3$+CD$_3$OD) δ 7.75 (d, J=8.0 Hz, 1H), 7.63-7.59 (m, 2H), 7.36-7.32 (m, 1H), 6.96 (s, 1H), 6.88 (d, J=8.0 Hz, 1H), 6.76 (d, J=8.4, 1H) 4.68 (s, 2H, —CH$_2$—), 3.80 (s, 3H, —OCH$_3$), 3.79 (s, 3H, —OCH$_3$). $^{13}$C-NMR (100 MHz, CDCl$_3$+CD$_3$OD) δ 160.8, 157.5, 150.3, 149.0, 148.6, 133.5, 130.2, 126.9, 126.2, 121.5, 120.7, 113.3, 112.0, 111.2, 55.9 (OCH$_3$), 55.8 (OCH$_3$), 45.2 (—CH$_2$—). LC-MS (ESI, formic) m/z: 330.1 ([M+H]$^+$).

8d was then obtained by following the general procedure. A solution of 7d (45 mg, 0.14 mmol) in n-BuOH (3 mL) was treated with DIEA (34.7 mg, 0.27 mmol) and L-prolinol (28 mg, 0.27 mmol). Compound 8d was purified from this crude material by prep-HPLC (UV 254 nm, 4.0 mL/min, H$_2$O/ACN (0.01% TFA) 5-60%, 0-30 min), (33.2 mg, 62.0%). purity (99.82%); $^1$H-NMR (400 MHz, CDCl$_3$+CD$_3$OD) δ 7.98 (d, J=8.0 Hz, 1H), 7.34 (brs, 2H), 7.10-7.08 (m, 1H), 7.0 (brs, 1H), 6.93 (d, J=8.0 Hz, 1H), 6.81 (d, J=8.0 Hz, 1H), 4.66-4.62 (m, 2H), 4.30 (m, 1H), 3.89 (s, 3H), 3.85 (s, 3H), 3.77 (dd, J=11.6, 4.4 Hz, 2H), 3.67 (m, 2H), 2.16-2.12 (m, 1H), 2.10-1.90 (m, 3H). $^{13}$C-NMR (100 MHz, CDCl$_3$+CD$_3$OD) δ 159.0, 149.1, 148.6, 134.6, 130.0, 124.4, 123.5, 120.7, 117.2, 111.8, 111.1, 109.5, 64.3, 61.0, 56.0, 55.0, 45.2, 28.9, 22.7. LC-MS (ESI, formic) m/z: 395.2 ([M+H]$^+$). HRMS (FAB) calcd for C$_{22}$H$_{27}$N$_4$O$_3$ ([M+H]$^+$) m/z: 395.2083, found m/z: 395.2076.

9d was then obtained by following the general procedure. A solution of 7d (45 mg, 0.14 mmol) in n-BuOH (3 mL) was treated with DIEA (35 mg, 0.27 mmol) and 2-piperidinethanol (31 mg, 0.27 mmol). Compound 9d was purified from this crude material by prep-HPLC (UV 254 nm, 4.0 mL/min, H$_2$O/ACN (0.01% TFA) 5-60%, 0-30 min), (25.3 mg, 45.6%). purity (99.36%); $^1$H-NMR (400 MHz, CD$_3$OD) δ 8.14 (dd, J=8.0, 0.8 Hz, 1H), 7.80 (t, J=8.4, 1.2 Hz, 1H), 7.63 (d, J=8.4 Hz, 1H), 7.46 (t, J=8.4, 1.2 Hz, 1H), 7.05 (d, J=2.0 Hz, 1H), 6.99 (dd, J=8.0, 2.0 Hz, 1H), 6.93 (d, J=8.4 Hz, 1H), 4.85 (d, J=, 2H), 3.99 (dd, J=11.6, 9.2 Hz, 1H), 3.84 (s, 3H), 3.85 (s, 3H), 3.76 (m, 1H), 3.28 (m, 1H), 1.98-1.85 (m, 2H), 1.81-1.68 (m, 3H), 1.68-1.51 (m, 1H). $^{13}$C-NMR (100 MHz, CD$_3$OD) δ 161.0, 154.1, 150.7, 150.1, 140.9, 136.3, 131.9, 126.2, 124.6, 121.4, 118.4, 116.8, 113.2, 112.9, 111.3, 61.0, 56.6, 55.5, 46.3, 41.8, 30.7, 26.2, 26.1, 24.2, 20.0. LC-MS (ESI, formic) m/z: 409.2 ([M+H]$^+$). HRMS (FAB) calcd for C$_{23}$H$_{28}$N$_4$O$_3$ ([M+H]$^+$) m/z: 409.2240, found m/z: 409.2242.

7c was then obtained by taking a solution of compound 3 (100 mg, 0.56 mmol) in n-BuOH (3 mL) and was then treated with DIEA (215.9 mg, 1.67 mmol) and 4-methoxybenzylamine (68.9 mg, 0.56 mmol). The resulting mixture was stirred for 2 h at 40° C. and the solvent was evaporated. The residue was extracted with methylene chloride (30 mL, 3 times) and water. The organic layer was dried over Na$_2$SO$_4$ and evaporated. Compound 7c was purified from this crude material by column chromatography (silicagel, n-hexane/EtOAc=3:1) (137.2 mg, 81.7%). $^1$H NMR (400 MHz, CDCl$_3$) δ 7.78-7.76 (m, 1H), 7.72 (ddd, J=8.4, 6.8, 1.2 Hz, 1H), 7.65 (d, 8.4 Hz, 1H), 7.42 (ddd, J=8.4, 6.8, 1.6 Hz, 1H), 7.35-7.31 (m, 2H), 6.09 (br s, 1H), 4.78 (d, J=5.2 Hz, 2H), 3.81 (s, 3H). $^{13}$C NMR (100 MHz, CDCl$_3$) δ 160.6, 159.5, 157.8, 150.9, 133.5, 129.8, 129.3, 127.9, 126.2, 120.8, 114.3, 113.2, 55.4, 45.3. LC-MS (ESI, formic) m/z 300.1 [M+H]$^+$.

8c was then obtained by taking a solution of 4i (80 mg, 0.27 mmol) in n-BuOH (4 mL) and was then treated with DIEA (69 mg, 0.54 mmol) and L-prolinol (54.0 mg, 0.54 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 9c was purified from this crude material by column chromatography (silicagel, CH$_2$Cl$_2$:MeOH=20:1) (62.3 mg, 63.4%). purity (97.50%); $^1$H-NMR (400 MHz, CDCl$_3$): δ 7.51 (d, J=8.4 Hz, 1H), 7.42-7.28 (m, 2H), 7.24 (d, J=8.8 Hz, 2H), 6.94 (td, J=8.0, 0.8 Hz, 1H), 6.79 (d, J=8.4 Hz, 2H), 4.70-4.58 (m, 2H), 4.25 (m, 1H), 3.80 (m, 1H), 3.72 (s, 3H), 3.66 (dd, J=10.8, 2.4 Hz, 1H), 3.59 (dd, J=11.2, 9.2 Hz, 1H), 3.53 (m, 1H), 2.10-2.00 (m, 1H), 1.94-1.72 (m, 2H), 1.65-1.55 (m, 1H). $^{13}$C-NMR (100 MHz, CDCl$_3$): δ 162.9, 162.2, 159.5, 159.0, 157.9, 133.0, 130.7, 129.2, 123.8, 121.4, 121.3, 114.0, 110.2, 68.0, 60.8, 55.3, 48.5, 44.6, 29.7, 23.9. HRMS (FAB) calculated for C$_{21}$H$_{25}$N$_4$O$_2$ ([M+H]$^+$) m/z: 365.1978, found m/z: 365.1971.

9c was then obtained by taking a solution of 4i (50 mg, 0.167 mmol) in n-BuOH (2 mL) and was then treated with DIEA (64.7 mg, 0.5 mmol) and 2-piperidinemethanol (55.77 mg, 0.48 mmol). The reaction mixture was stirred overnight at 120° C. and the solvent was evaporated. The residue was extracted with methylene chloride (20 mL, 3 times) and water. The organic layer was dried over Na$_2$SO$_4$ and evaporated. Compound 9c was purified from this crude material by column chromatography (silicagel, CH$_2$Cl$_2$:MeOH:triethylamine=10:1:0.1) (46.8 mg, 74.0%). purity (96.28%); $^1$H NMR (400 MHz, CDCl$_3$) δ 7.50-7.39 (m, 3H), 7.32 (d, J=8.4 Hz, 2H), 7.03-6.99 (m, 1H), 6.90-6.86 (m, 2H), 5.90 (br s, 1H), 5.29 (s, 2H), 5.06-5.00 (m, 1H), 4.77 (d, J=15.2 Hz, 1H), 4.75-4.64 (m, 2H), 4.07 (t, J=10.4, 10.0 Hz, 1H), 3.80 (s, 3H), 3.73 (dd, J=10.8, 4.0 Hz, 1H), 3.20-3.13 (m, 1H), 1.73-1.51 (m, 6H). $^{13}$C NMR (100 MHz, CDCl$_3$) δ 160.5, 159.5, 159.1, 132.7, 130.7, 129.2, 125.4, 121.1, 120.7, 114.1, 110.5, 64.3, 55.3, 53.4, 53.4, 44.8, 39.9, 26.4, 25.3, 20.2. HRMS (FAB) calculated for C$_{22}$H$_{27}$N$_4$O$_2$ ([M+H]$^+$) m/z 379.2134, found m/z 379.2141; mp 175.5-179.2.

R-9c was generated from (R)-2-piperidinemethanol using the same procedure as for compound 9c. Purity (99.66%); $^1$H NMR (400 MHz, DMSO-d$_6$) δ 11.75 (br, 1H), 9.97 (s, 1H), 8.27 (d, J=6.0 Hz, 1H), 7.81-7.73 (m, 2H), 7.34-7.44 (m, 3H), 6.90 (m, 2H), 4.72 (d, J=3.6 Hz, 1H), 3.63 (s, 3H), 3.60 (m, 1H), 3.17 (m, 1H), 1.85-1.57 (m, 6H). $^{13}$C-NMR (100 MHz, CDCl$_3$+CD$_3$OD) δ 159.2, 159.1, 152.6, 139.4, 134.7, 129.3, 129.2, 129.1, 124.6, 122.8, 117.7, 114.0, 109.6, 60.1, 55.2, 54.6, 44.9, 40.2, 25.2, 24.9, 18.9. HRMS (FAB) calculated for C$_{22}$H$_{27}$N$_4$O$_2$ ([M+H]$^+$) m/z 379.2134, found m/z 379.2132. [α]$_D^{20}$ 0.281 (c 0.3, CH$_3$OH).

S-9c was generated from S)-2-piperidinemethanol using the same procedure as for compound 9c. Purity (99.19%); $^1$H NMR (400 MHz, DMSO-d$_6$) δ 11.78 (br, 1H), 9.97 (s, 1H), 8.28 (d, J=6.0 Hz, 1H), 7.82-7.72 (m, 2H), 7.35-7.43 (m, 3H), 6.92 (m, 2H), 4.73 (d, J=3.6 Hz, 1H), 3.65 (s, 3H), 3.60 (m, 1H), 3.18 (m, 1H), 1.82-1.56 (m, 6H). $^{13}$C-NMR (100 MHz, CDCl$_3$+CD$_3$OD) δ 159.5, 158.8, 133.4, 130.4, 128.9, 122.3, 122.2, 121.8, 113.9, 110.3, 61.7, 55.2, 53.5, 44.5, 40.1, 25.5, 25.0, 19.5. HRMS (FAB) calculated for C$_{22}$H$_{27}$N$_4$O$_2$ ([M+H]$^+$) m/z: 379.2134, found m/z: 379.2136. [α]$_D^{20}$ −0.052 (c 0.3, CH$_3$OH).

Cell Culture

INS-1 cells were cultured in RPMI 1640 (Corning, N.Y., USA) supplemented with 10% FBS (Atlanta Biologicals, Norcross, Ga.), HEPES (10 mM, Life Technologies, CA, USA), sodium pyruvate (1 mM, Corning), 2-mercaptoethanol (50 μM, Sigma, St Louis, Mo., USA) and antibiotics (100 UI/mL penicillin and 100 μg/mL streptomycin, Corning). βTC6 cells were cultured in DMEM (Corning) with 15% FBS, sodium pyruvate (1 mM, Corning), non-essential amino acids (1 mM, Thermo, IL, USA), GlutaMAX (1 mM, Life Technologies) and antibiotics (100 UI/mL penicillin and 100 μg/mL streptomycin). Human islets were obtained from the Integrated Islet Distribution Program (Duarte, Calif.) in accordance with Oklahoma Medical Research Foundation's internal review board (IRB) and ethical guidelines for the use of human tissue. Standard viability was 80-90% and purity was >80%. Islets were maintained in CMRL medium (Life Technologies) supplemented with 10% FBS. All cells were grown at 37° C. in a humidified 5% $CO_2$ atmosphere.

Cell Survival Assay

INS-1 cells or βTC6 cells were seeded at $3 \times 10^3$ cells/well in a 384-well plate and treated with compounds at the indicated concentrations. After 3 d treatment, the medium was aspirated and 20 μL/well of CellTiter-Glo reagent (Promega, WI, USA) was added for the detection of intracellular ATP levels. Cell viability was measured with an EnVision multilabel plate reader (PerkinElmer, MA, USA).

RNA Isolation and qRT-PCR

INS-1 cells were seeded at $4 \times 10^5$ cells/well in 6-well plates and treated with compounds for the indicated times. Total RNA was extracted using TRIzol reagent (Invitrogen, Carlsbad, Calif.) according to the manufacturer's protocol, and 2 μg of total RNA was reverse transcribed using a Superscript kit (Invitrogen). Real-time PCR was performed in 96-well format using SYBR Select Master Mix (Applied Biosystems, Foster City, Calif.) with an ABI 7500 PCR system (Applied Biosystems). The primer sequences used are shown in U.S. Ser. No. 62/542,408, Aug. 8, 2107.

Western Blotting

INS-1 cells were seeded in 60-mm dishes at $8 \times 10^5$ cells/dish and treated for the indicated times. Cells were then washed with PBS and lysed with lysis buffer (Cell Signaling Technology, Danvers, Mass.) containing EDTA (Thermo, IL) and phosphatase inhibitors (Thermo). Aliquots of 20 μg total protein were separated on 7% SDS-PAGE gels (Life Technologies) and transferred to PVDF membranes (Life Technologies). The membranes were probed with primary antibodies followed by the appropriate HRP-conjugated secondary antibodies (goat anti-rabbit IgG and goat anti-mouse IgG, 1:3000; Santa Cruz Biotechnology, CA, USA). Blots were then developed. The primary antibodies and dilutions used were: CHOP (1:1000, MA1-250, Thermo), ATF4 (1:1000, 10835-1-AP, ProteinTech Group, IL, USA), cleaved caspase 3 (1:1000, 9661, Cell Signaling Technology, MA, USA), PARP (1:1000, 9542L, Cell Signaling Technology), and α-tubulin (1:3000, SC-8035, Santa Cruz Biotechnology).

MTT Assay

INS-1 cells or βTC6 cells were seeded at $3 \times 10^3$ cells/well in a 384-well plate and treated with compounds at the indicated concentrations. After 3 d treatment, the medium was aspirated and 10 μl of MTT reagent (Cayman Chemical, MI, USA, prepared according to manufacturer's instruction) to each well was added and mixed gently for one minute on an orbital shaker. The cells were then incubated for three hours at 37° C. in a $CO_2$ incubator. After incubation, add 100 μl of crystal dissolving solution to each well, and incubate for 4 hours in a 37° C. $CO_2$ incubator. Viability will be measured for the absorbance to each sample at 570 nm using EnVision multilabel plate reader (PerkinElmer, MA, USA).

Glucose-Stimulated Insulin Secretion

INS-1 or primary human islet cells were plated in 96-well plates. The second day, Tm and compound 9c were added and maintained for 24 h (INS-1) or 48 h (human islets). Cells were then incubated in fresh KRBH buffer (115 mM NaCl, 5 mM KCl, 24 mM $NaHCO_3$, 2.5 mM $CaCl_2$, 1 mM $MgCl_2$, 10 mM HEPES, 2% w/v BSA, pH 7.4) containing 2.5 mM glucose for 1 h. Cells were incubated for an additional hour in KRBH buffer containing 2.5, 25 (for INS-1 cells), or 20 (for human islets) mM glucose. The secreted insulin was measured with insulin ELISA kits (for mouse insulin from Millipore and for human insulin from LifeTech). Cells were lysed with RIPA buffer (50 mM Tris HCl pH 7.4, 1% NP-40, 0.25% sodium deoxycholate, 150 mM NaCl), and total cellular protein was determined with a Bradford protein assay. The secreted insulin levels were corrected for total protein.

Immunofluorescent and TUNEL Staining

Primary human islets were washed with PBS and fixed with 4% paraformaldehyde for 30 min. Fixed cells were then blocked in 5% normal donkey serum for 30 min. Polyclonal guinea pig anti-insulin (A0564, Dako, 1:500 dilution) was used as primary antibody. Donkey Cy3 anti-guinea pig IgG was used as the secondary antibody. TUNEL staining was performed with In Situ Cell Death Detection Kit-Fluorescein (Roche) according to the manufacturer's instructions. DAPI was used for nuclear counter-staining. Images were taken with an Olympus FV1000 confocal microscope.

Statistical Analysis

Data are presented as means±SD unless specified. Comparisons were performed by two-tailed paired Student's t-test. A P value of <0.05 was considered statistically significant.

In accordance with the foregoing, the present disclosure is directed, in at least some embodiments, to the following:

Clause 1. A compound having a formula as represented by chemical structure I:

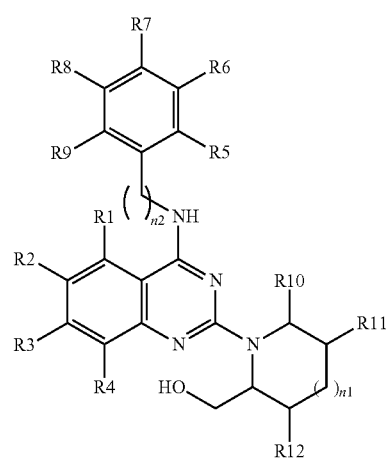

wherein:

$R_1$-$R_{12}$ are independently selected from the group consisting of hydrogen (H), hydroxyl (OH), chlorine (Cl), fluorine (F), bromine (Br), alkyl, alkoxy, haloalkyl, haloalkoxyl; and n1=0-1 and n2=1-4.

Clause 2. The compound of clause 1, wherein n1 is zero or one.

Clause 3. The compound of clause 1, wherein n2 is one or two or three or four.

Clause 4. The compound of clause 1, wherein at least one of $R_7$, $R_8$, and $R_9$ is an alkyl Clause 5. The compound of clause 1, wherein at least one of $R_7$, $R_8$, and $R_9$ is a methyl Clause 6. The compound of clause 1, wherein at least one of $R_7$, $R_8$, and $R_9$ is an ethyl Clause 7. The compound of clause 1, wherein at least one of $R_7$, $R_8$, and $R_9$ is an alkoxy Clause 8. The compound of clause 1, wherein at least one of $R_7$, $R_8$, and $R_9$ is an methoxy Clause 9. The compound of clause 1, wherein at least one of $R_7$, $R_8$, and $R_9$ is an ethoxy Clause 10. The compound of clause 1, wherein at least one of $R_7$, $R_8$, and $R_9$ is a haloalkyl Clause 11. The compound of clause 1, wherein at least one of $R_7$, $R_8$, and $R_9$ is an monohaloalkyl Clause 12. The compound of clause 1, wherein at least one of $R_7$, $R_8$, and $R_9$ is an dihaloalkyl Clause 13. The compound of clause 1, wherein at least one of $R_7$, $R_8$, and $R_9$ is an trihaloalkyl.

Clause 14. The compound of clause 1, wherein at least one of $R_7$, $R_8$, and $R_9$ is an haloalkoxyl.

Clause 15. The compound of clause 1, wherein at least one of $R_7$, $R_8$, and $R_9$ is an monohaloalkoxyl.

Clause 16. The compound of clause 1, wherein at least one of $R_7$, $R_8$, and $R_9$ is an dihaloalkoxyl.

Clause 17. The compound of clause 1, wherein at least one of $R_7$, $R_8$, and $R_9$ is an trihaloalkoxyl.

Clause 18. A composition comprising a pharmaceutically-acceptable carrier, diluent or vehicle, and the compound of any of clauses 1-17.

Clause 19. The composition of clause 18 further comprising one or more targeting molecules linked to the pharmaceutically acceptable carrier, vehicle, or diluent, or to the compound having chemical structure I, wherein the one or more targeting molecules are able to bind to a target cell or a portion of a target cell.

Clause 20. The composition of clause 19, wherein the target cell is a pancreatic β-cell.

Clause 21. A method of ameliorating a symptom associated with type 1 or type 2 diabetes in a subject in need of such therapy, comprising: administering to the subject an effective amount of the compound or composition of any one of clauses 1-20.

Clause 22. A use of the compound or composition of any one of clauses 1-20 for ameliorating a symptom associated with type 1 or type 2 diabetes in a subject, comprising administering to the subject an effective amount of said compound or composition.

Clause 23. A method of protecting pancreatic β cells from ER stress-induced dysfunction in a subject in need of such therapy, comprising: administering to the subject an effective amount of the compound or composition of any one of clauses 1-20.

Clause 24. A use of the compound or composition of any one of clauses 1-20 for protecting pancreatic β cells from ER stress-induced dysfunction in a subject, comprising administering to the subject an effective amount of said compound or composition.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various compounds and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A compound having a formula as represented by chemical structure I:

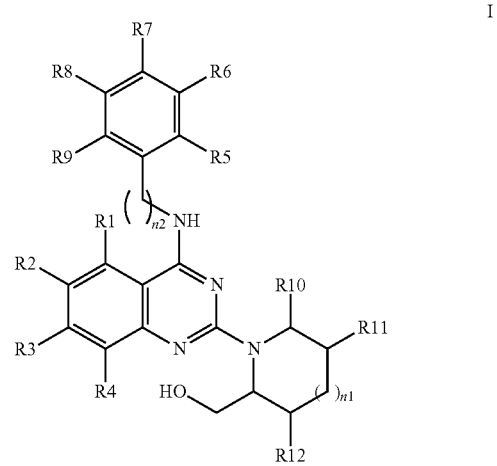

wherein:

$R_1$-$R_{12}$ are independently selected from the group consisting of hydrogen (H), hydroxyl (OH), chlorine (Cl), fluorine (F), bromine (Br), alkyl, alkoxy, haloalkyl, and haloalkoxyl, with the proviso that at least one of $R_7$, $R_8$, and $R_9$ is a haloalkyl; and n1=0 or 1 and n2=1, 2, 3, or 4.

2. The compound of claim 1, wherein the at least one haloalkyl of $R_7$, $R_8$, and $R_9$ is a monohaloalkyl.

3. The compound of claim 1, wherein the at least one haloalkyl of $R_7$, $R_8$, and $R_9$ is a dihaloalkyl.

4. The compound of claim 1, wherein the at least one haloalkyl of $R_7$, $R_8$, and $R_9$ is a trihaloalkyl.

5. A composition comprising a pharmaceutically-acceptable carrier, diluent or vehicle, and the compound of claim 1.

6. A compound having a formula as represented by chemical structure I:

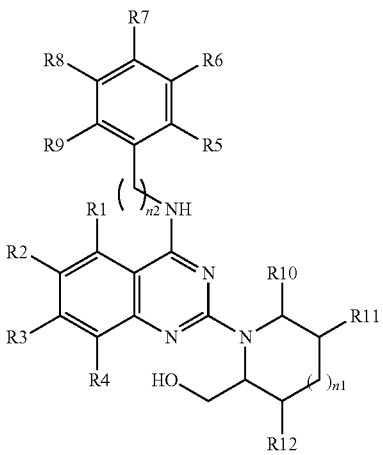

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and haloalkoxyl;
n1=1; and
n2=1, 2, 3, or 4, and wherein at least one of R$_7$, R$_8$, and R$_9$ is a haloalkyl or haloalkoxyl.

7. A conjugate, comprising the compound of claim 1 and a targeting molecule, wherein the targeting molecule is able to bind to a target cell or a portion of a target cell.

8. The conjugate of claim 7, wherein the target cell is a pancreatic β-cell.

9. A conjugate, comprising a compound and a targeting molecule, wherein the targeting molecule is able to bind to a target cell or a portion of a target cell and the compound has a formula as represented by chemical structure I:

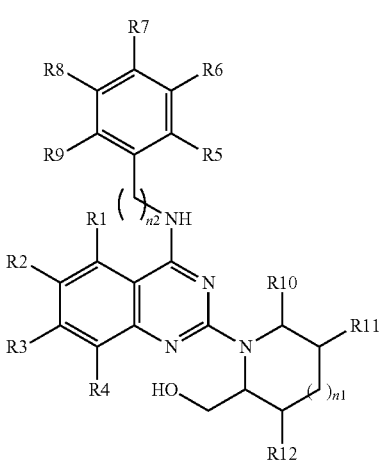

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and haloalkoxyl;
n1=0 or 1; and
n2=1, 2, 3, or 4; with the proviso that when n1=0, n2=1, and when n1=1, n2=1, 2, 3, or 4.

10. The conjugate of claim 9, wherein the target cell is a pancreatic β-cell.

11. The conjugate of claim 9, wherein at least one of R$_7$, R$_8$, and R$_9$ is an alkyl.

12. The conjugate of claim 9, wherein at least one of R$_7$, R$_8$, and R$_9$ is an alkoxyl.

13. The conjugate of claim 9, wherein at least one of R$_7$, R$_8$, and R$_9$ is a haloalkyl.

14. The conjugate of claim 9, wherein at least one of R$_7$, R$_8$, and R$_9$ is a haloalkoxyl.

15. A conjugate, comprising a compound bound to a targeting molecule, wherein the targeting molecule is able to bind to a target cell or a portion of a target cell and wherein the compound has a formula as represented by chemical structure I:

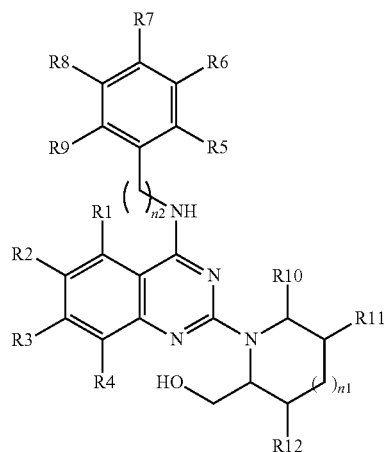

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and haloalkoxyl;
n1=1; and
n2=1, 2, 3, or 4.

16. The conjugate of claim 15, wherein at least one of R$_7$, R$_8$, and R$_9$ is an alkyl.

17. The conjugate of claim 15, wherein at least one of R$_7$, R$_8$, and R$_9$ is an alkoxyl.

18. The conjugate of claim 15, wherein at least one of R$_7$, R$_8$, and R$_9$ is a haloalkyl.

19. The conjugate of claim 15, wherein at least one of R$_7$, R$_8$, and R$_9$ is a haloalkoxyl.

20. The conjugate of claim 15, wherein the target cell is a pancreatic β-cell.

21. A method of treating a condition associated with abnormal cell function related to endoplasmic reticulum (ER) stress, comprising: administering, to a subject having said condition, an effective amount of a compound having a formula as represented by chemical structure I:

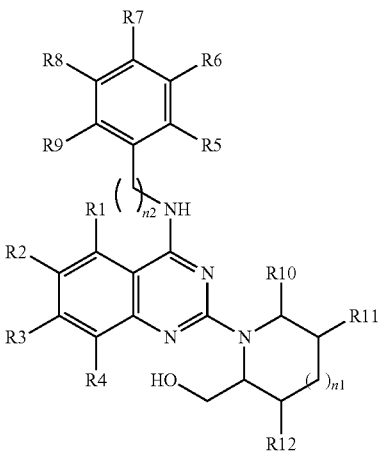

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and, haloalkoxyl, with the proviso that at least one of R$_7$, R$_8$, and R$_9$ is a haloalkyl; and
n1=0 or 1 and n2=1, 2, 3, or 4.

22. The method of claim 21, wherein the condition associated with abnormal cell function is type 1 or type 2 diabetes.

23. The method of claim 21, wherein the treatment protects pancreatic β cells from ER stress-induced dysfunction.

24. A method of treating a condition associated with abnormal cell function related to endoplasmic reticulum (ER) stress, comprising:
administering, to a subject having said condition, an effective amount of a compound having a formula as represented by chemical structure I:

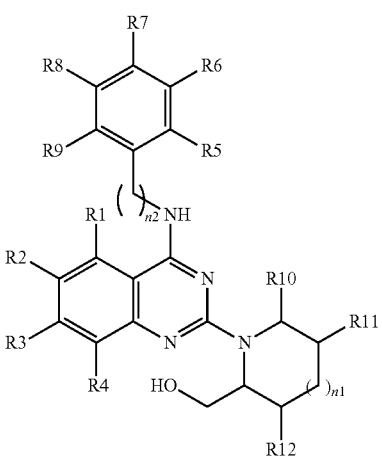

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and haloalkoxyl;

n1=1; and
n2=1, 2, 3, or 4, and wherein at least one of R$_7$, R$_8$, and R$_9$ is a haloalkyl or haloalkoxyl.

25. The method of claim 24, wherein the condition associated with abnormal cell function is type 1 or type 2 diabetes.

26. The method of claim 24, wherein the treatment protects pancreatic β cells from ER stress-induced dysfunction.

27. A method of treating a condition associated with abnormal cell function related to endoplasmic reticulum (ER) stress, comprising:
administering, to a subject having said condition, an effective amount of a conjugate comprising a compound and a targeting molecule, wherein the targeting molecule is able to bind to a target cell or a portion of a target cell, and the compound has a formula as represented by chemical structure I:

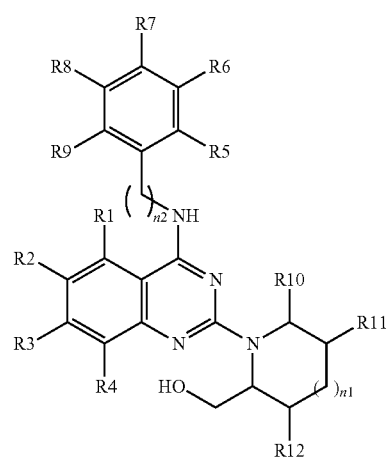

wherein:
R$_1$-R$_{12}$ are independently selected from the group consisting of hydrogen (H), hydroxyl (OH), chlorine (Cl), fluorine (F), bromine (Br), alkyl, alkoxy, haloalkyl, and haloalkoxyl;
n1=1; and
n2=1, 2, 3, or 4.

28. The method of claim 27, wherein the condition associated with abnormal cell function is type 1 or type 2 diabetes.

29. The method of claim 27, wherein the treatment protects pancreatic β cells from ER stress-induced dysfunction.

30. The method of claim 27, wherein at least one of R$_7$, R$_8$, and R$_9$ is an alkyl.

31. The method of claim 27, wherein at least one of R$_7$, R$_8$, and R$_9$ is an alkoxyl.

32. The method of claim 27, wherein at least one of R$_7$, R$_8$, and R$_9$ is a haloalkyl.

33. The method of claim 27, wherein at least one of R$_7$, R$_8$, and R$_9$ is a haloalkoxyl.

34. The method of claim 27, wherein the target cell is a pancreatic β-cell.

* * * * *